United States Patent
Shah et al.

(10) Patent No.: US 11,253,207 B2
(45) Date of Patent: Feb. 22, 2022

(54) SYSTEMS AND METHODS FOR MEDICAL MONITORING

(71) Applicant: Neopenda, PBC, Chicago, IL (US)

(72) Inventors: Sona Shah, Chicago, IL (US); Teresa Cauvel, Chicago, IL (US); Rebecca Peyser, Teaneck, NJ (US)

(73) Assignee: Neopenda, PBC, Chicago, IL (US)

( * ) Notice: Subject to any disclaimer, the term of this patent is extended or adjusted under 35 U.S.C. 154(b) by 0 days.

(21) Appl. No.: 16/323,120

(22) PCT Filed: Aug. 8, 2017

(86) PCT No.: PCT/US2017/045944
§ 371 (c)(1),
(2) Date: Feb. 4, 2019

(87) PCT Pub. No.: WO2018/031570
PCT Pub. Date: Feb. 15, 2018

(65) Prior Publication Data
US 2019/0159739 A1    May 30, 2019

Related U.S. Application Data

(60) Provisional application No. 62/372,661, filed on Aug. 9, 2016.

(51) Int. Cl.
*A61B 5/00* (2006.01)
*A61B 5/01* (2006.01)
(Continued)

(52) U.S. Cl.
CPC ............ *A61B 5/746* (2013.01); *A61B 5/0008* (2013.01); *A61B 5/0022* (2013.01); *A61B 5/01* (2013.01);
(Continued)

(58) Field of Classification Search
CPC .............. A61B 5/02438; A61B 5/6831; A61B 5/02055; A61B 5/74; G08B 21/0453;
(Continued)

(56) References Cited

U.S. PATENT DOCUMENTS

| | | | | |
|---|---|---|---|---|
| 2007/0100666 A1* | 5/2007 | Stivoric | ............... | A61B 5/6833 705/3 |
| 2008/0051667 A1* | 2/2008 | Goldreich | .......... | A61B 5/02055 600/481 |
| 2008/0077020 A1* | 3/2008 | Young | .................. | A61B 5/0205 600/484 |
| 2008/0214903 A1* | 9/2008 | Orbach | .................. | G06Q 50/22 600/301 |

(Continued)

FOREIGN PATENT DOCUMENTS

| | | |
|---|---|---|
| CN | 101828908 A | 9/2010 |
| CN | 104055499 A | 9/2014 |

(Continued)

OTHER PUBLICATIONS

International Search Report and Written Opinion dated Nov. 17, 2017, in corresponding International Application No. PCT/US2017/045944 (10 pages).

*Primary Examiner* — Gary Jackson
*Assistant Examiner* — Zahed Kabir
(74) *Attorney, Agent, or Firm* — Bookoff McAndrews, PLLC

(57) ABSTRACT

A medical device includes a temperature sensor configured to deliver a temperature signal and an optical sensor configured to deliver an optical signal. The medical device also includes a microcontroller configured to receive the temperature signal and the optical signal. The microcontroller is configured to calculate, in real-time, a body temperature, a pulse rate, a respiratory rate, and a blood oxygen concentration based on the received temperature signal and the received optical signal. The medical device also includes a display configured to display the body temperature, the pulse rate, the respiratory rate, and the blood oxygen concentration of a patient.

20 Claims, 11 Drawing Sheets

(51) Int. Cl.
*A61B 5/0205* (2006.01)
*A61B 5/1455* (2006.01)
*G08B 21/04* (2006.01)
*G08B 21/18* (2006.01)
*A61B 5/08* (2006.01)
*A61B 5/024* (2006.01)
*G16H 40/67* (2018.01)

(52) U.S. Cl.
CPC ...... *A61B 5/02055* (2013.01); *A61B 5/02416* (2013.01); *A61B 5/02438* (2013.01); *A61B 5/0816* (2013.01); *A61B 5/14551* (2013.01); *A61B 5/6804* (2013.01); *A61B 5/725* (2013.01); *A61B 5/7257* (2013.01); *A61B 5/7278* (2013.01); *A61B 5/743* (2013.01); *A61B 5/747* (2013.01); *A61B 5/7425* (2013.01); *A61B 5/7475* (2013.01); *G08B 21/0453* (2013.01); *G08B 21/182* (2013.01); *G16H 40/67* (2018.01); *A61B 5/02427* (2013.01); *A61B 5/6814* (2013.01); *A61B 5/6831* (2013.01); *A61B 5/74* (2013.01); *A61B 2560/0214* (2013.01)

(58) Field of Classification Search
CPC ... B65D 63/1018; A44B 17/0035; A45F 5/02; F16G 11/101
See application file for complete search history.

(56) References Cited

U.S. PATENT DOCUMENTS

| | | | |
|---|---|---|---|
| 2009/0018421 A1* | 1/2009 | Sarussi | A61B 5/6814 600/324 |
| 2010/0241018 A1* | 9/2010 | Vogel | A61B 5/0002 600/511 |
| 2011/0066010 A1* | 3/2011 | Moon | A61B 5/742 600/301 |
| 2012/0029300 A1* | 2/2012 | Paquet | G06F 19/3418 600/300 |
| 2014/0163425 A1* | 6/2014 | Tran | G16Z 99/00 600/595 |
| 2015/0112168 A1 | 4/2015 | Conrad et al. | |
| 2015/0305632 A1* | 10/2015 | Najarian | A61B 5/7207 600/301 |
| 2016/0345915 A1* | 12/2016 | Jain | A61B 5/747 |
| 2018/0177459 A1* | 6/2018 | Eletr | A61B 5/0002 |

FOREIGN PATENT DOCUMENTS

| | | |
|---|---|---|
| EP | 0875199 A1 | 11/1998 |
| JP | 2007-020971 A | 2/2007 |
| JP | 2008-061663 A | 3/2008 |
| JP | 2008-293301 A | 12/2008 |
| JP | 2009-060969 A | 3/2009 |
| JP | 2015-100673 A | 6/2015 |

* cited by examiner

SYSTEMS AND METHODS FOR MEDICAL MONITORING

CROSS-REFERENCE TO RELATED APPLICATIONS

This application is the U.S. national phase entry under 35 U.S.C. § 371 of International Application No. PCT/US2017/045944, filed on Aug. 8, 2017, which claims priority to U.S. Patent Application No. 62/372,661, filed on Aug. 9, 2016.

TECHNICAL FIELD

Various aspects of the present disclosure relate generally to systems and methods useful in monitoring one or more patients.

BACKGROUND OF THE DISCLOSURE

Many hospitals and medical care providers have insufficient resources, are understaffed, and/or are overwhelmed with patients. Hospitals and medical care providers in many developing countries, for example, often lack sufficient equipment, skilled technicians, and stable power supplies. As such, hospitals and medical care providers in many developing countries often experience disproportionally high neonatal mortality rates. In some aspects, mortality rates may be reduced if care is provided at a first indication of distress, such as, e.g., one or more abnormal vital signs of a patient. Often times, however, insufficient equipment, time, and/or an inconsistent power supply reduces the medical professional's ability to continuously and reliably monitor the vital signs for each patient. Therefore, health issues and even deaths may be prevented if a device or system allows the medical professionals to continuously monitor the vital signs for each patient and signal if and when a patient is exhibiting an abnormal vital sign and/or other indication of distress.

The systems, devices, and methods of the current disclosure may rectify some of the deficiencies described above, and/or address other aspects of the prior art.

SUMMARY OF THE DISCLOSURE

Examples of the present disclosure relate to, among other things, medical systems, devices, and methods. Each of the examples disclosed herein may include one or more of the features described in connection with any of the other disclosed examples.

In one example, a medical device may include a temperature sensor configured to deliver a temperature signal and an optical sensor configured to deliver an optical signal. The medical device also may include a microcontroller configured to receive the temperature signal and the optical signal. The microcontroller may be configured to calculate, in real-time, a body temperature, a pulse rate, a respiratory rate, and a blood oxygen concentration based on the received temperature signal and the received optical signal. The medical device also may include a display configured to display the body temperature, the pulse rate, the respiratory rate, and the blood oxygen concentration of a patient.

Examples of the medical device may additionally include any one or more of the following features. In one aspect, the medical device may calculate, in real-time, the body temperature, the pulse rate, the respiratory rate, and the blood oxygen concentration based only on the received temperature signal and the received optical signal. The microcontroller may be configured to signal an alert if the body temperature, the pulse rate, the respiratory rate, or the blood oxygen concentration is outside of a preset range. The medical device may further include a transmitter unit. The transmitter unit may be configured to transmit signals over a Bluetooth low energy network to at least one of a user device, a server, or a database. The medical device may be coupled to a garment. A strap may be coupled to the medical device via at least one attachment portion. The medical device may further include at least one indicator light. The microcontroller may be powered by a battery, and the medical device may further include a battery level indicator.

In another aspect, a medical system may include a plurality of medical devices, a first medical device of the plurality of medical devices being configured to be positioned proximate skin of a first patient, and a second medical device of the plurality of medical devices being configured to be positioned proximate skin of a second patient. Each of the plurality of medical devices may be configured to obtain patient-specific biometric data in real-time. The system may also include a user device, and each of the plurality of medical devices and the user device may transmit and receive signals via a low energy network.

Examples of the medical system may additionally include any one or more of the following features. The user device may include a user interface with a dashboard, and the dashboard may display the patient-specific biometric data received from the plurality of medical devices. The dashboard may display at least one of a body temperature, pulse rate, respiratory rate, and blood oxygen concentration for each patient. At least one of the plurality of medical devices and the user device may include a threshold or range for each patient-specific biometric data measurement. If the patient-specific biometric data measurement exceeds or is outside of the respective threshold or range, then at least one of a medical device of the plurality of medical devices and the user device may indicate an alert. The alert may be an indicator light on the medical device. The alert may be an audible alarm signaled on the user device. The alert may also be sent to an additional device via the low energy network or as an SMS signal.

According to another aspect, a method may include acquiring patient-specific biometric data from a plurality of wearable medical devices, with each wearable medical device being positioned on a patient. Each wearable medical device may include a sensor positioned proximate skin of the patient, and the sensor may acquire the patient-specific biometric data in real-time. The method may also include processing the data acquired from the sensor and determining whether the processed data is within a defined threshold or range. If the processed data is not within the defined threshold or range, the method may include signaling an alert.

Examples of the method may additionally include any one or more of the following features. The method may further include, if the processed data is within the defined threshold or range, continuing to acquire data from the sensor. The alert may be signaled on a wearable device. The alert may be signaled on a user device.

In a further example, a medical device may consist of a temperature sensor configured to deliver a temperature signal and an optical sensor configured to deliver an optical signal. The medical device also may consist of a microcontroller configured to receive the temperature signal and the optical signal. The microcontroller may be configured to calculate, in real-time, a body temperature, a pulse rate, a respiratory rate, and a blood oxygen concentration based on the received temperature signal and the received optical signal. The medical device also may consist of a display configured to display the body temperature, the pulse rate, the respiratory rate, and the blood oxygen concentration of a patient.

Both the foregoing general description and the following detailed description are exemplary and explanatory only and are not restrictive of the features, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." It should be noted that all numeric values disclosed or claimed herein (including all disclosed values, limits, and ranges) may have a variation of +/−10% (unless a different variation is specified) from the disclosed numeric value. Moreover, in the claims, values, limits, and/or ranges of various claimed elements and/or features means the stated value, limit, and/or range +/−10%.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments. There are many aspects and embodiments described herein. Those of ordinary skill in the art will readily recognize that the features of a particular aspect or embodiment may be used in conjunction with the features of any or all of the other aspects or embodiments described in this disclosure.

DETAILED DESCRIPTION

Embodiments of the present disclosure include systems, devices, and methods to facilitate and improve the efficacy and safety of patient monitoring. For example, aspects of the present disclosure may provide a user (e.g., a physician, medical technician, a parent or guardian monitoring a baby or child, or other medical service provider) with the ability to monitor one or more patients. Such monitoring may be based on patient-specific information. Additionally, the systems, devices, and methods of the present disclosure may facilitate the issuing of one or more alerts so as to notify a user of a patient's vital sign status.

Reference now will be made in detail to examples of the present disclosure described above and illustrated in the accompanying drawings. Wherever possible, the same reference numbers will be used throughout the drawings to refer to the same or like parts.

Figure 1:
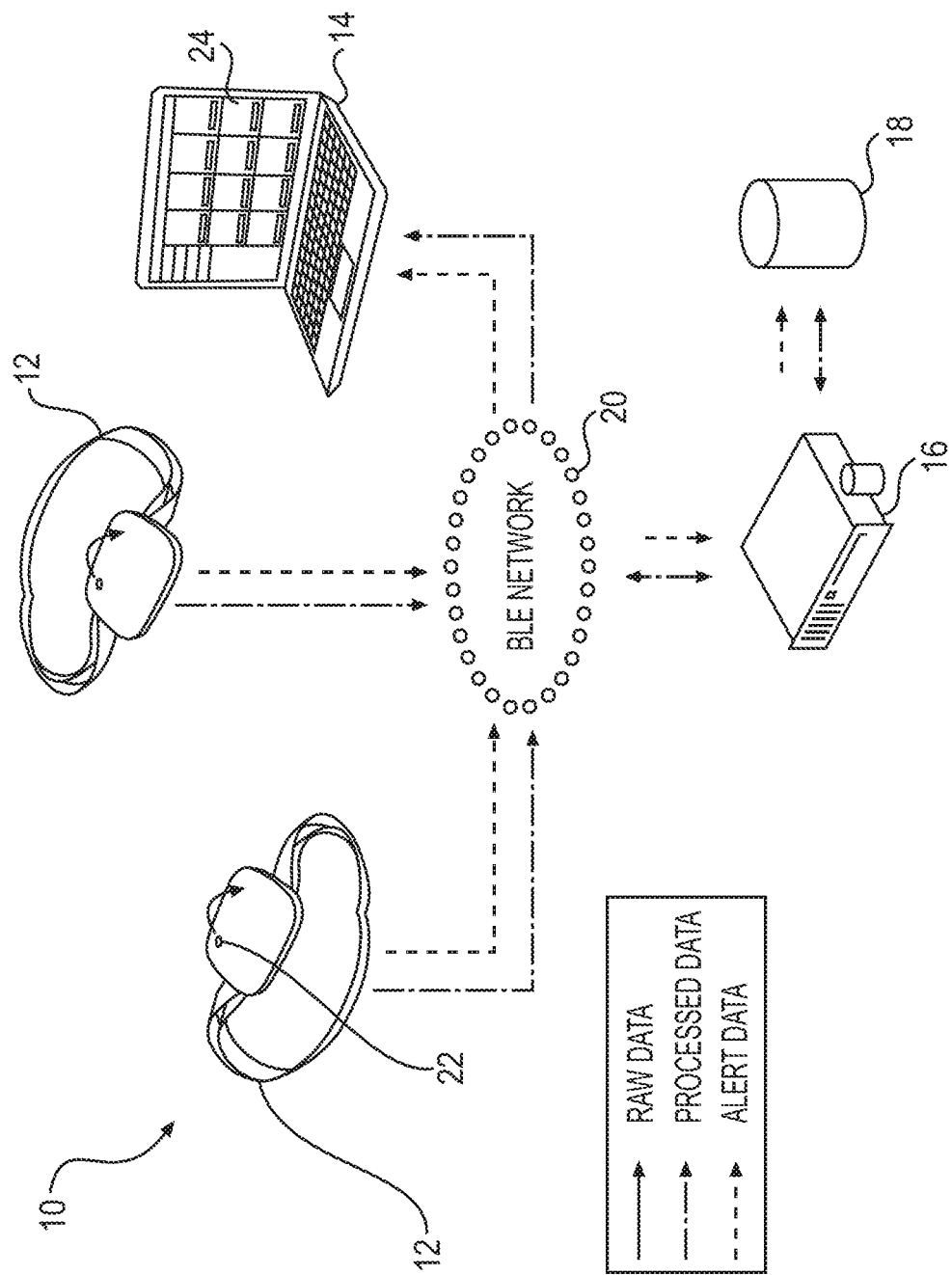
FIG. 1 illustrates a medical system, according to aspects of the present disclosure.

FIG. 1 illustrates a system 10 including at least one wearable device 12 and a user device 14. System 10 may also include a server 16 and a database 18. While server 16 and database 18 are illustrated as separate elements, the disclosure is not so limited. Rather, in some arrangements, server 16 and database 18 may be incorporated into user device 14, and/or combined into a separate device. As shown in FIG. 1, each wearable device 12 may sense raw data and process that raw data to obtain processed data and/or alert data. The processed data and/or the alert data may then be sent, for example, via a Bluetooth Low Energy ("BLE") network 20, to one or more of user device 14, server 16, and/or database 18. Based on the processed data and/or the alert data, one or both of wearable device 12 and user device 14 may indicate an alert or warning. The alert or warning may be displayed via an indicator 22 on wearable device 12 and/or on a display 24 of user device 14.

Figure 2:
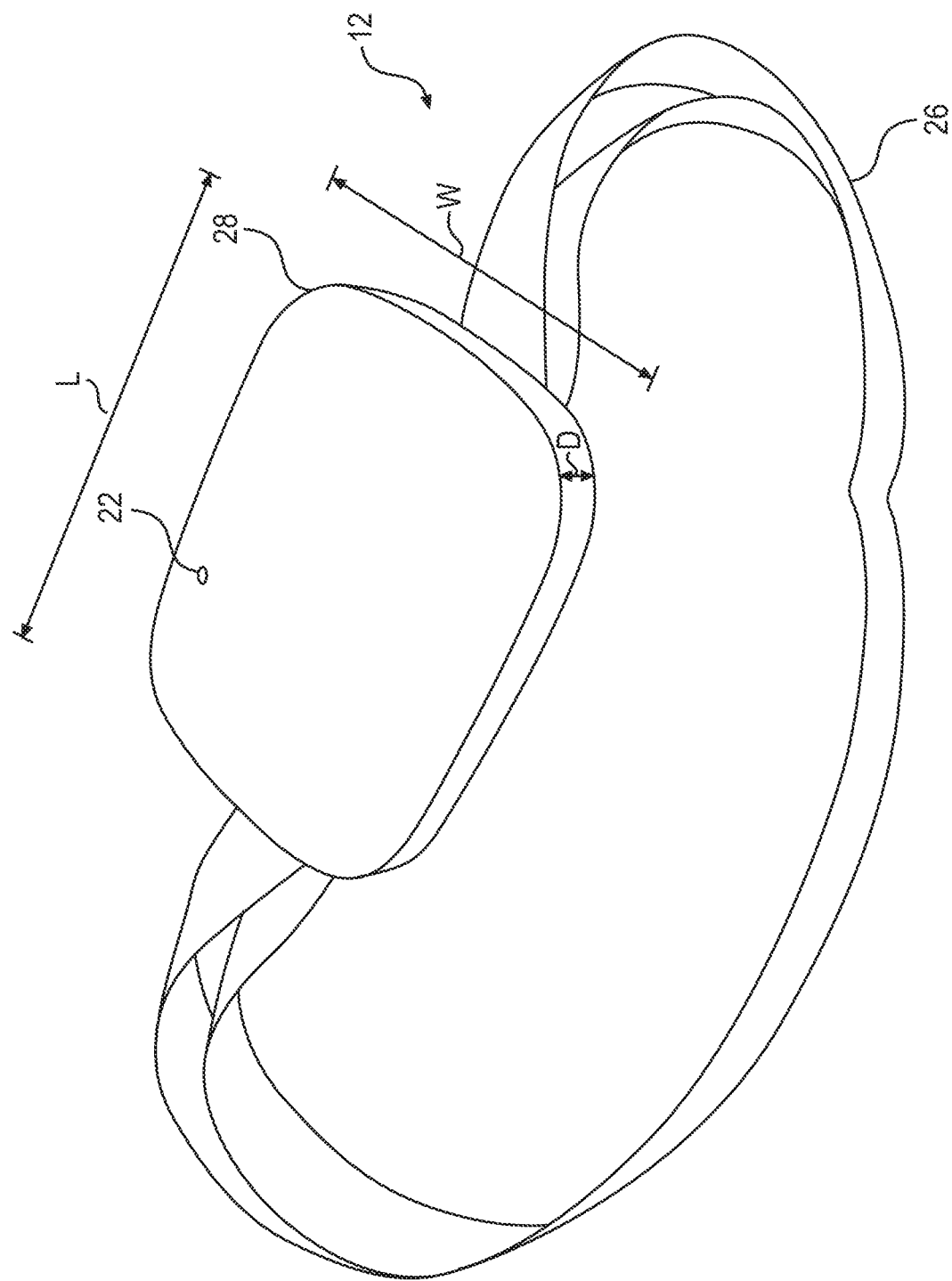
FIG. 2 illustrates a perspective view of an exemplary wearable device, according to aspects of the present disclosure.

As shown in FIGS. 1 and 2, wearable device 12 may be positioned on a patient using a band or strap 26. Wearable device 12 may be removably coupled to strap 26, or may be formed with strap 26 being integrated into a housing 28 of wearable device 12. Housing 28 may be coupled to strap 26 such that strap 26 attaches to housing 28 on a side opposite to indicator 22. Housing 28 may be fully enclosed and may include rounded or otherwise chamfered edges, which may aid in cleaning and improve safety. In one aspect, housing 28 may have a length L between about 70 mm and about 80 mm, or approximately 75 mm long. In other arrangements, housing 28 may have a length L between about 40 mm and about 45 mm, or approximately 43 mm. Additionally, housing 28 may have a width W between about 50 mm and about 60 mm, or approximately 56 mm wide. In other arrangements, housing 28 may have a width W of between about 30 mm and about 40 mm, or approximately 32 mm. Further, housing 28 may have a depth D between about 10 mm and about 15 mm, or approximately 13 mm deep.

Housing 28 may include a seal (not shown) to ensure housing 28 is at least partially water-resistant. Housing 28 may also include a small valve, which may be made of Gore-tex® material. The valve may aid in allowing for equilibration in pressure between the sealed housing 28 and its outside environment to prevent pressure build up in high elevations or under heating. Housing 28 may comprise a heat-resistant plastic material, not susceptible to UV light. Housing 28 may also be resistant to bleach and/or other medical grade cleaning products. For example, housing 28 may be formed of a PA 2201 polyamide natural medical grade nylon polymer, compliant with the appropriate FDA and EU medical device regulations. Alternatively, housing 28 may be comprised Radel® polyphenylsulfone (PPSU), XENOY™ resin, and/or any other appropriate material or combinations thereof. Housing 28 may also be able to withstand sanitization with 70% isopropyl alcohol.

Strap 26 may be adjustable to couple housing 28 to different body parts (e.g., foot, wrist, upper arm, chest, head, etc.) and to different sized patients. In some arrangements, a single patient may simultaneously wear multiple wearable devices 12 coupled to various body parts. Strap 26 may be textured and/or have gripping capabilities to aid in ensuring that strap 26 and wearable device 12 retain their position when mounted on a patient. Strap 26 may be reusable and cleanable, or strap 26 may be disposable. If reusable, strap 26 may be eco-friendly, lead-free, BPA-free, PVC-free, and meet the requirements of the Consumer Product Safety Improvement Act of 2008. For example, strap 26 may be made of a MiniTwist Silicone Doodle Placemat. If disposable, strap 26 may be soft-touch, plastic-free, non-porous, BPA-free, PVC-free, lead-free, latex-free, phthalate-free, may be cleanable with soap and water, and may be made of FDA and EU approved food-grade silicone. For example, strap 26 may be a Neat Solutions® Tidy Topper® Disposable Multi-Use Pad. Strap 26 may be at least partially elastic and safe for contact with sensitive skin. Moreover, strap 26 may be able to withstand sanitization with 70% isopropyl alcohol and/or bleach. Additional details of strap 26 will be described in connection with FIG. 6.

User device 14 may be any electronic display device, e.g., a laptop computer, a desktop computer, a tablet, smartphone, smartwatch, pager, etc. User device 14 may include display 24, which may be a screen or a touch screen. Display 24 conveys information regarding at least one patient wearing/coupled to wearable device 12. In one aspect, display 24 may display information regarding at least five wearable devices 12, at least fifteen wearable devices 12, at least thirty wearable devices 12, etc. Display 24 may display the processed data and/or alert data received from each of the wearable devices 12 being monitored.

In one aspect, user device 14 may include a mobile application, which may be downloadable or preloaded. The application may include a capability to connect to BLE network 20 to transmit and receive information and signals to and from other elements of system 10. As discussed in more detail below, the application may sort and store information for each wearable device 12, individual user profiles, historical data, and include other features. The application on user device 14 may also transmit and receive data to and from server 16 and database 18.

Furthermore, while user device 14 is illustrated as a single computer (e.g., laptop computer), the disclosure is not so limited. Rather, user device 14 may include two devices, for example, a laptop computer and a smartwatch, pager, tablet, or other such portable device. The laptop computer may receive, process, and display information (e.g., via display 24) obtained from the at least one wearable device 12. If an alert is signaled, the alert may be displayed on display 24 (or an audible signal may be emitted from) the laptop computer and a signal may be transmitted to the smartwatch, pager, tablet, or other such portable device to better ensure the user is apprised of the alert regardless of whether the user is within a specified range of the laptop computer display 24 and/or close enough to hear auditory alerts from the laptop computer. In one aspect, the alert may be transmitted from the laptop computer to the smartwatch, pager, tablet, or other such portable device as an SMS message or over any communications network, including BLE network 20. It is understood that the second device may be a user's smartphone, and any alert information may be selectively displayed on both the laptop computer display 24 and the smartphone. The information displayed on display 24 may be transmitted to the laptop computer and then to the smartphone, or may be directly transmitted to both the laptop computer and the smartphone.

Server 16 may include at least one processor to process data obtained by the at least one wearable device 12. Database 18 may store data obtained from the at least one wearable device 12, and may also store patient-specific or user-specific settings. As mentioned above, both server 16 and database 18 may be incorporated into user device 14. Server 16 or database 18 may also be cloud based modules, which may provide for more efficient or effective data processing and storage. Alternatively, cloud based modules may serve as backup databases in the event of a local malfunction or loss of power.

BLE network 20 may be a wireless personal area network which does not require an internet connection. BLE network may be any short range personal area network to exchange data using short-wavelength UHF radio waves. BLE network 20 may require low power levels, may have a range of approximately 20-30 m or more indoors and approximately 60-80 m or more outdoors. BLE network 20 may also include proximity location capabilities and may automatically connect or pair known devices in system 10 when the devices are within a specific range of each other. The devices may be identified by unique device serial numbers, MAC addresses, radio-frequency identification codes, etc.

It is noted that while Bluetooth communication networks are discussed, the elements of system 10 may also transmit and receive signals and data over any known or later developed communication system. For example, the elements of system 10 may transmit and receive signals and data over WiFi, a cellular network, SMS messaging, or any other wired or wireless protocol.

Figure 3:
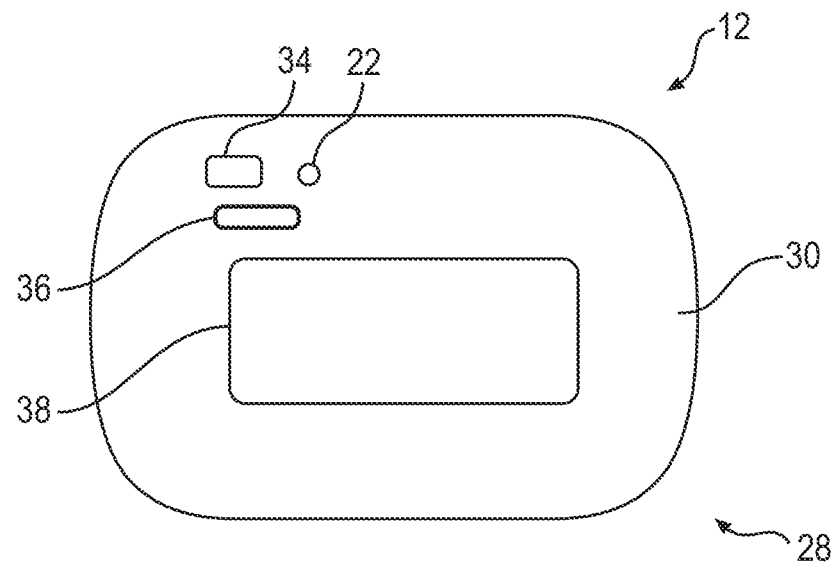
FIG. 3 illustrates a plan view of a front portion of an exemplary wearable device, according to aspects of the present disclosure.
Figure 4:
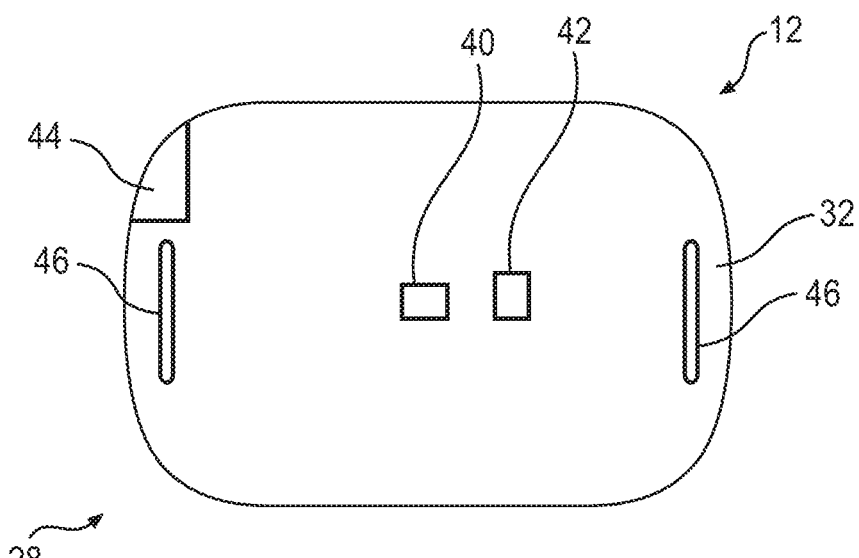
FIG. 4 illustrates a plan view of a back portion of the exemplary wearable device of FIG. 3, according to aspects of the present disclosure.

As shown in FIGS. 3 and 4, housing 28 of wearable device 12 includes a front portion 30 and a back portion 32. When positioned on a patient, front portion 30 is configured to face outward (e.g., away from the patient), and back portion 32 is configured to face and/or contact the patient's skin. Further, front portion 30 and back portion 32 may be coupled to one another in any appropriate manner. For example, front portion 30 and back portion 32 may be snap-fit, friction fit, and/or coupled together via one or more mechanical fasteners (e.g., screws, etc., not shown). Alternatively, front portion 30 and back portion 32 may be coupled to one another via covering 58 (FIG. 5), without departing from the scope of the disclosure.

Front portion 30 may include indicator 22, as noted above. Front portion 30 may also include a power button 34, e.g., an on/off button, a battery level indicator 36, and optionally, a display 38. Power button 34 may also include an LED or other illumination element to indicate whether wearable device 12 is powered on or off. Battery level indicator 36 may indicate the status and/or charge level of an internal battery 54 (FIG. 5), which may be rechargeable or replaceable. For example, battery level indicator 36 may be a segmented or continuous bar that indicates the current amount of power and/or time remaining for the battery to power wearable device 12. Display 38 may be an LCD display, and may visually indicate patient status, patient identifying information, etc. Display 38 may be a touch screen, and optionally, indicator 22, power button 32, battery level indicator 36 may be incorporated in display 38. Although not shown, front portion 30 may also include other indicators or inputs such as, for example, a reset button.

Figure 5:
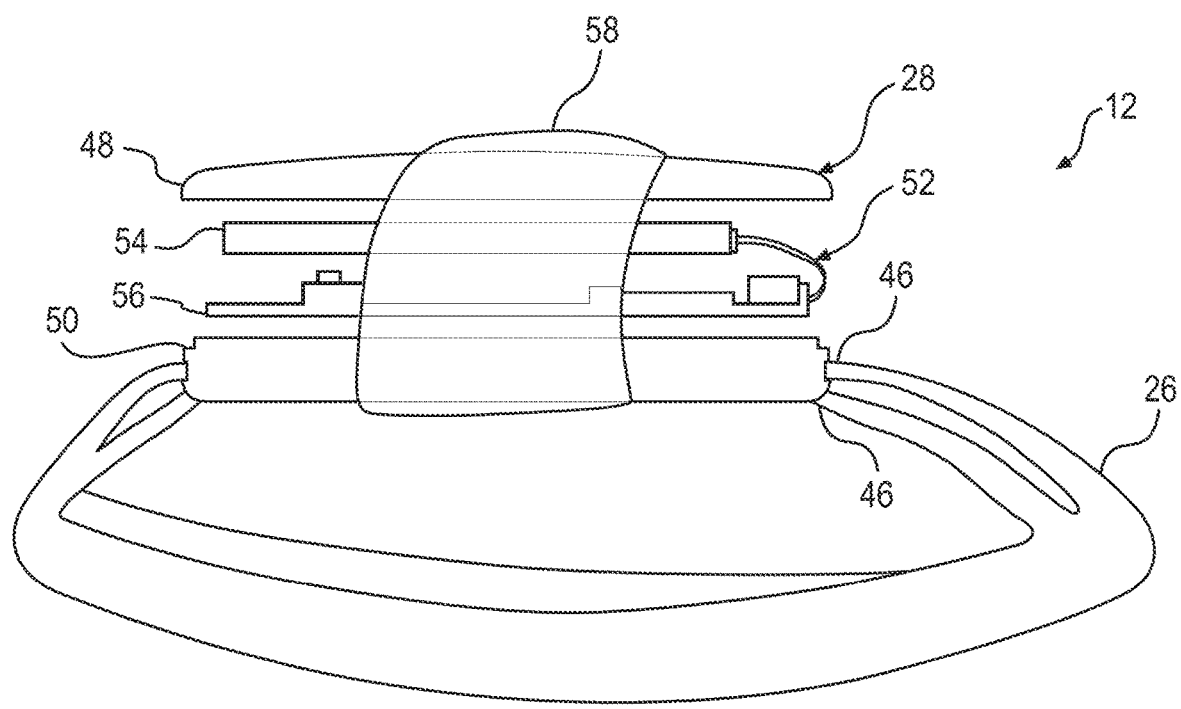
FIG. 5 illustrates a partially exploded view of the exemplary wearable device of FIGS. 3 and 4, according to aspects of the present disclosure.

Back portion 32 may include a temperature sensor 40 and an optical sensor 42. Both temperature sensor 40 and optical sensor 42 may be positioned to face and/or contact a patient's skin when wearable device 12 is positioned on a patient. In one aspect, when positioned on a patient, back portion 32, temperature sensor 40, and optical sensor 42 may be in contact with the patient's skin. In another aspect, when positioned on the patient, any of back portion 32, temperature sensor 40, and optical sensor 42 may be proximate to the patient's skin, for example, 0.5 mm, 1 mm, 3 mm, 5 mm, or 10 mm away from the patient's skin. Back portion 32 also may include a charging port 44, for example, to charge the internal rechargeable battery 54 through a wired connection (FIG. 5). Back portion 32 may include slots 46 positioned proximate to opposing sides of back portion 32, and slots 46 may allow for strap 26 to attach to housing 28 via threading strap 26 through slot 46. Slots 46 may be perpendicular to a longitudinal axis of housing 28. In other arrangements, however, slots 46 need not be perpendicular to the longitudinal axis of housing 28. Slots 46 may also internally connect/align to slots (not shown) on the sides of housing 28 or front portion 30 of housing 28 such that strap 26 may be threaded into one of slots 46 and out of another slot on a side of housing 28 or though front portion 30. Alternatively, back portion 32 may include Velcro, hooks, or any other elements to attach strap 26 or another garment to housing 28. Although not shown, back portion 32 may include a memory card port, for example, an SD card port, to operably couple a memory card to wearable device 12.

Temperature sensor 40 may be a thermistor or any suitable sensor for external use. Temperature sensor 40 may detect the patient's body temperature, thus indicative of a fever, hyperthermia, hypothermia, etc. Temperature sensor 40 may transmit signals and information to user device 14, server 16, and database 18 through BLE network 20. In one aspect, the raw data of measurements of temperature sensor 40 may be directly transmitted to at least one of user device 14, server 16, and database 18 through BLE network 20, with the data being analyzed by at least one of user device 14, server 16, and database 18. In another aspect, as shown in FIG. 1, the raw data measurements of temperature sensor 40 may be analyzed by internal components (e.g., processor) within wearable device 12, with the processed and/or alert data then being transmitted to at least one of user device 14, server 16, and database 18 through BLE network 20. Based on the data, one or more of wearable device 12, user device 14, server 16, and database 18 may signal an alert.

Optical sensor 42 may include both a light emitting element, for example, an LED emitting a safe wavelength and intensity of light, and a light detecting element. Optical sensor 42 may emit a certain amount of light (e.g., ultraviolet, visible, or infrared light) from the light emitting element (e.g., an LED), and based on the amount of light reflected by the patient's skin and detected by the light detecting element, optical sensor 42 may measure the patient's pulse rate, respiratory rate, and blood oxygen saturation (e.g., $SpO_2$ or peripheral capillary oxygen saturation). Alternatively, optical sensor 42 may be based on transmittance through a patient's skin. For example, a light emitting element may be positioned on one side of a patient's finger or toe, and a light detecting element may be positioned on the opposing side of the patient's finger or toe. Based on the amount of light transmitted through the patient's finger or toe and detected by the light detecting element, optical sensor 42 may measure the patient's pulse rate, respiratory rate, and blood oxygen saturation (e.g., $SpO_2$ or peripheral capillary oxygen saturation).

In one example, optical sensor 42 may include a red light source and an infrared light source, along with a corresponding red light detecting element and an infrared light detecting element. The red light and the infrared light may penetrate, reflect, and/or transmit to different depths and/or in different ways. In one aspect, the red light and/or the infrared light may be used to perform photoplethysmography to determine volumetric changes in the blood. As with the temperature sensor 40, the data obtained by optical sensor 42 may be analyzed by internal components (e.g., a processor) within wearable device 12, with the processed and/or alert date then transmitted to at least one of user device 14, server 16, and database 18 through BLE network 20. Alternatively, the raw data of measurements of optical sensor 42 may be directly transmitted to at least one of user device 14, server 16, and database 18 through BLE network 20, with the data being analyzed by at least one of user device 14, server 16, and database 18. Based on the data received from optical sensor 42, one or more of wearable device 12, user device 14, server 16, and database 18 may signal an alert.

Optical sensor 42 may include a light barrier, which may block ambient light from interfering with the measurements of optical sensor 42. For example, optical sensor 42 and/or the shape of housing 28 may block light in a radius of approximately 2 cm from optical sensor 42. Such a light barrier may include 3D printed Accura SL 5530 material with a black dye, which may or may not include a post-cure thermal treatment.

FIG. 5 illustrates a partially exploded view of wearable device 12 with housing 28 attached to strap 26. As shown, housing 28 includes a front case 48 (or front portion 30, FIG. 3) and a back case 50 (or back portion 32, FIG. 4). Similar to front portion 30 and back portion 32, described above, front case 48 and back case 50 may be coupled to one another in any appropriate manner, such as, e.g., snap-fit, friction fit, and/or via one or more mechanical fasteners (e.g., screws, etc., not shown). Additionally or alternatively, front case 48 and back case 50 may be coupled to one another via covering 58, without departing from the scope of the disclosure.

Back case 50 may include slots 46 to attach strap 26 to housing 28. Front case 48 and back case 50 may enclose a plurality of internal components 52 positioned between front portion 30 and back portion 32. Internal components 52 may include a battery 54 and a printed circuit board 56. Printed circuit board 56 may include a microcontroller and/or processor, a transmitter unit, a receiver unit, an antenna, and other electrical components to transmit signals to, and receive signals from indicator 22, battery level indicator 36, display 38, temperature sensor 40, optical sensor 42, and charging port 44. Printed circuit board 56 and the electrical components may be powered by battery 54. In one aspect, battery 54 may be a 3.7 V battery with a 700 mAh capacity, 450 mAh charge current, and a 14 mAh discharge current. Battery 54 may have a charge time of approximately 105 minutes and a runtime of approximately 50 hours. In one aspect, battery 54 may be rechargeable and may run for multiple days, for example 5-7 days, between charges.

Furthermore battery 54 may be charged by any suitable manner, including, for example, wired or wireless induction charging.

Alternatively or additionally, printed circuit board 56 and the electrical components may be powered using alternative power sources, for example, solar power. In one aspect, wearable device 12 may include battery 54, with battery 54 being rechargeable via a solar panel on or separate from wearable device 12. In another aspect, wearable device 12 may include a wired connection to an external power source, for example, a solar powered battery cell or a generator cell, in order for electrical power to be transferred to wearable device 12. Internal components 52 may also transmit and receive signals to and from user device 14, server 18, and/or database 18 through BLE network 20 or other wired or wireless systems.

As shown in FIG. 5, wearable device 12 may include a covering 58. Covering 58 may be, for example, a disposable plastic wrap. In some arrangements, covering 58 may remain on wearable device 12 during use, and may be transparent, allowing temperature sensor 40 and optical sensor 42 to obtain biometric data through covering 58. In this aspect, wearable device 12 may be used for different patients by changing covering 58 between patient uses. Covering 58 may provide additional insulation between each of temperature sensor 40 and optical sensor 42 and the skin of a patient. Additionally, covering 58 may cover, surround, or otherwise be positioned on only a portion of wearable device 12. For example, covering 58 may be wrapped only around a portion of wearable device 12.

Figure 6:
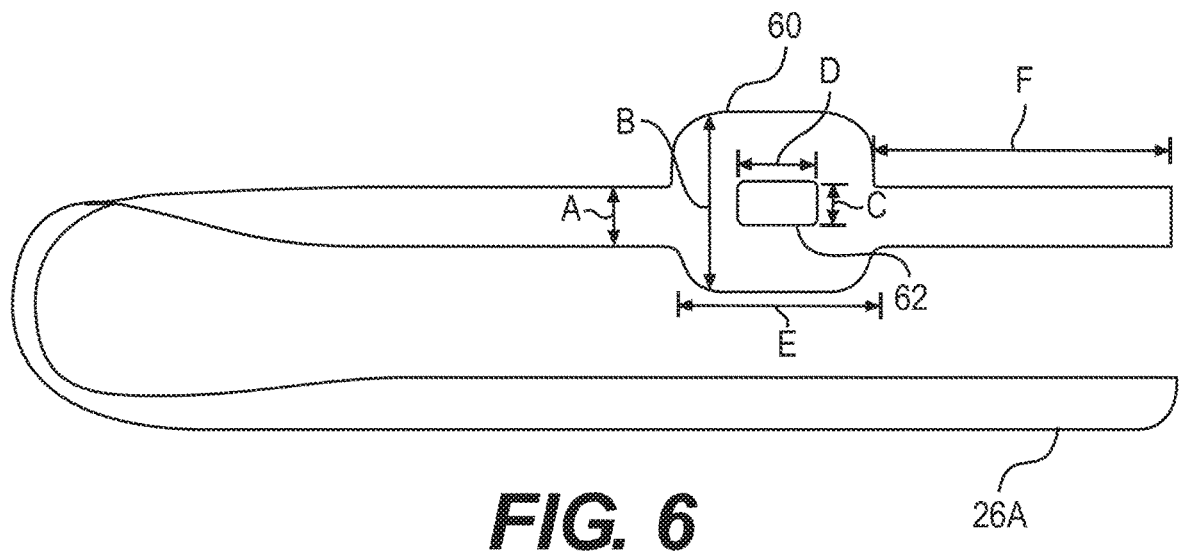
FIG. 6 illustrates a perspective view of an exemplary strap, according to aspects of the present disclosure.

FIG. 6 illustrates a perspective view of an alternative configuration of a strap 26A. Strap 26A includes a relatively wide portion 60 and an opening 62. Wide portion 60 may be shaped to correspond to the shape and size of housing 28. Opening 62 may be cut out in approximately the center of wide portion 60. Opening 62 may correspond to the position of temperature sensor 40 and optical sensor 42 to allow the sensors to face and/or contact the patient's skin without interference from strap 26A. Opening 62 may also include a transparent covering. Strap 26A may include Velcro, hooks, adhesive, or any other mechanism to attach housing 28 to wide portion 60 of strap 26A, and to adjustably secure strap 26A on or around a portion of a patient's body. Optionally, strap 26A may be threaded through one or more slots 46 of housing 28, as described above.

In some arrangements, strap 26A may have width A of between about 1 cm and about 2 cm, or about 1.75 cm, while portion 60 may have a width B between about 5 and about 6 cm, or about 5.4 cm. Additionally, opening 62 may include a width C of between about 1 cm and about 2 cm, or about 1.3 cm. A length D of opening 62 may be between about 2 cm and about 3 cm, or about 2.3 cm. Additionally, a length E of portion 60 may be between about 5 cm and about 7 cm, or about 6 cm. Further, a length F of strap 26A extending between one end portion 60 and an end of strap 26 may be between about 8 cm and about 9 cm, or about 8.3 cm. Additionally, a length of strap 26A extending from the opposite end of portion 60 and an end of strap 26 may be between about 50 cm and about 60 cm, or about 55 cm. In one aspect, strap 26A may be cut from a roll or sheet of reusable or disposable material. Strap 26A may be cut using a template shape. Furthermore, strap 26A and/or housing 28 may include or be coupled to a sensor insulation between temperature sensor 40 and optical sensor 42 and the patient's skin. The sensor insulation may be coupled to printed circuit board 56 within housing 28, or may be exterior to housing 28. In one aspect, sensor insulation may be disposable, such as, Glad® ClingWrap low density polyethylene film, which may also be BPA-free, non-PVC, and phthalate-free.

Figure 7:
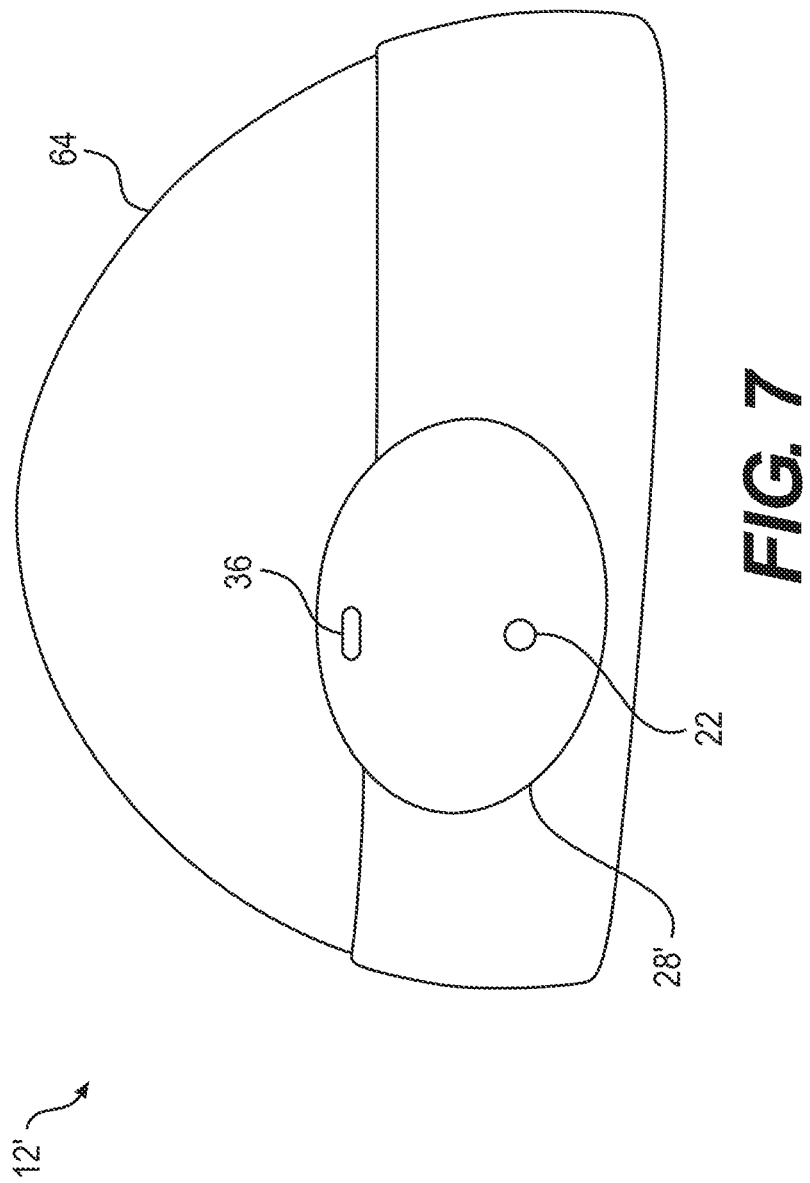
FIG. 7 illustrates a perspective view of an additional exemplary wearable device, according to aspects of the present disclosure

While examples of the present disclosure illustrate wearable device 12 coupled to strap 26 (or 26A), the disclosure is not so limited. Rather, in some arrangements, wearable device 12 may be mounted, coupled, or otherwise joined with any appropriate garment. For example, as shown in FIG. 7, a wearable device 12' may include a housing 28' embedded into or otherwise coupled to a garment, e.g., a hat 64. Similar to strap 26A discussed above, hat 64 may include an opening (not shown) such that the sensors of wearable device 12' on a back portion of housing 28' may face and/or contact the patient's skin without interference from the garment material. Alternatively, similar to strap 26, hat 64 may be coupled to sides of housing 28' such that the sensors may face and/or contact the patient's skin without interference from hat 64. Although only indicator 22 and battery level indicator 36 are shown in FIG. 7, wearable device 12' may include any one or more of the aforementioned features described in connection with FIGS. 2-5.

Figure 8:
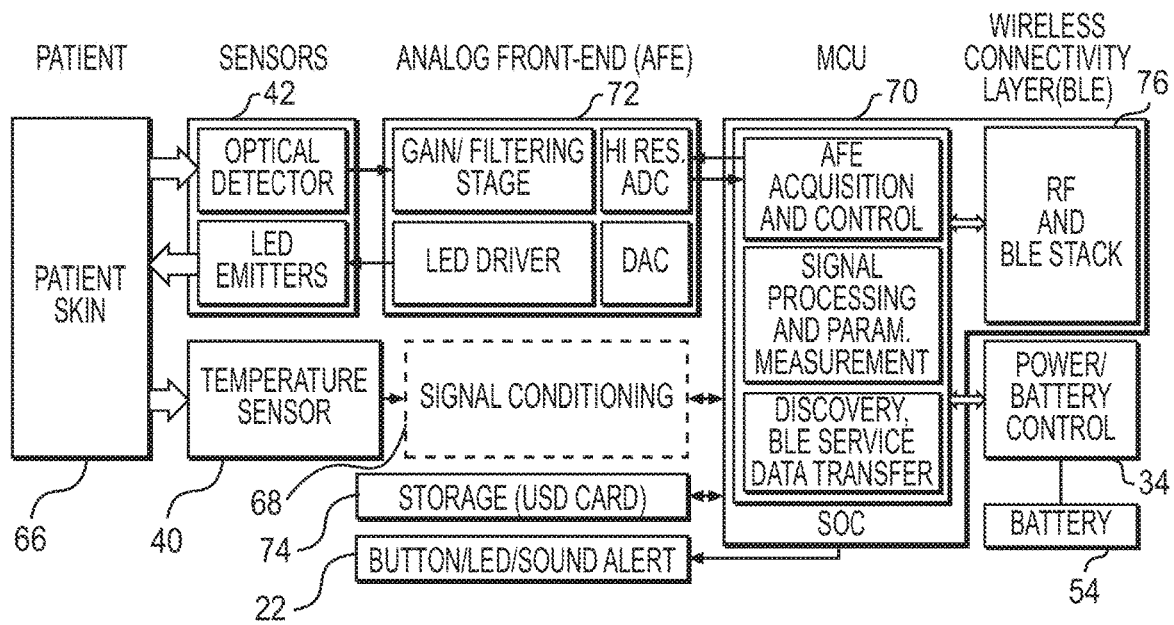
FIG. 8 illustrates an exemplary electronics structure, according to aspects of the present disclosure.

Referring now to FIG. 8, an exemplary functional architecture of wearable device 12 is illustrated. For example, temperature sensor 40 may detect a temperature of a patient's skin 66, and optical sensor 42, including one or more light emitting elements and one or more light detecting elements, may obtain data to detect the pulse rate, respiratory rate, and blood oxygen saturation for the patient. Temperature sensor 40 may transmit the obtained information to a signal conditioning unit 68, which may modulate the obtained information, and then transmit the information to a microcontroller unit ("MCU") 70. Optical sensor 42 may be operably connected to (or include therein) Analog Front-End ("AFE") 72, which may include an LED driver and a gain/filtering stage. The LED driver may power the LED emitter, and the obtained optical data may be transmitted to the gain/filtering stage within AFE 72. AFE 72 may also include a Digital-to-Analog Converter ("DAC") and a High Resolution Analog-to-Digital Converter ("ADC") to convert data obtained from optical sensor 42 and other signals received from other elements of system 10. AFE 72 may transmit and receive signals and data to and from MCU 70. As such, MCU 70 may include an AFE Acquisition and Control unit. MCU 70 may also include a Signal Processing and Parameter Measurement unit and a Discovery BLE Service Data Transfer. Lastly, MCU 70 may include a system on a chip ("SoC") (e.g., printed circuit board 56), and MCU 70 may be in communication with a storage unit 74 (e.g., a USD card), one or more input devices (e.g., power button 34 coupled to battery 54), and one or more output devices (e.g., indicator 22, battery level indicator 36, display 38, a sound alert, etc.).

Wearable device 12 may also include a wireless connectivity layer 76. Wireless connectivity layer 76 may be part of MCU 70 or be otherwise coupled to MCU 70 on printed circuit board 56 within wearable device 12. Wireless connectivity layer 76 may include a radio frequency and a BLE stack, such that wearable device 12 may transmit and receive data and signals to and from other elements of system 10 over BLE network 20 and/or over radio frequencies. Battery 54 and a power/battery control element (e.g., power button 34) may be coupled to and power MCU 70 and the electronic elements of wearable device 12. Battery 54 and power button 34 may also be coupled to the charging port 44 (not shown) to recharge battery 54.

Figure 9:
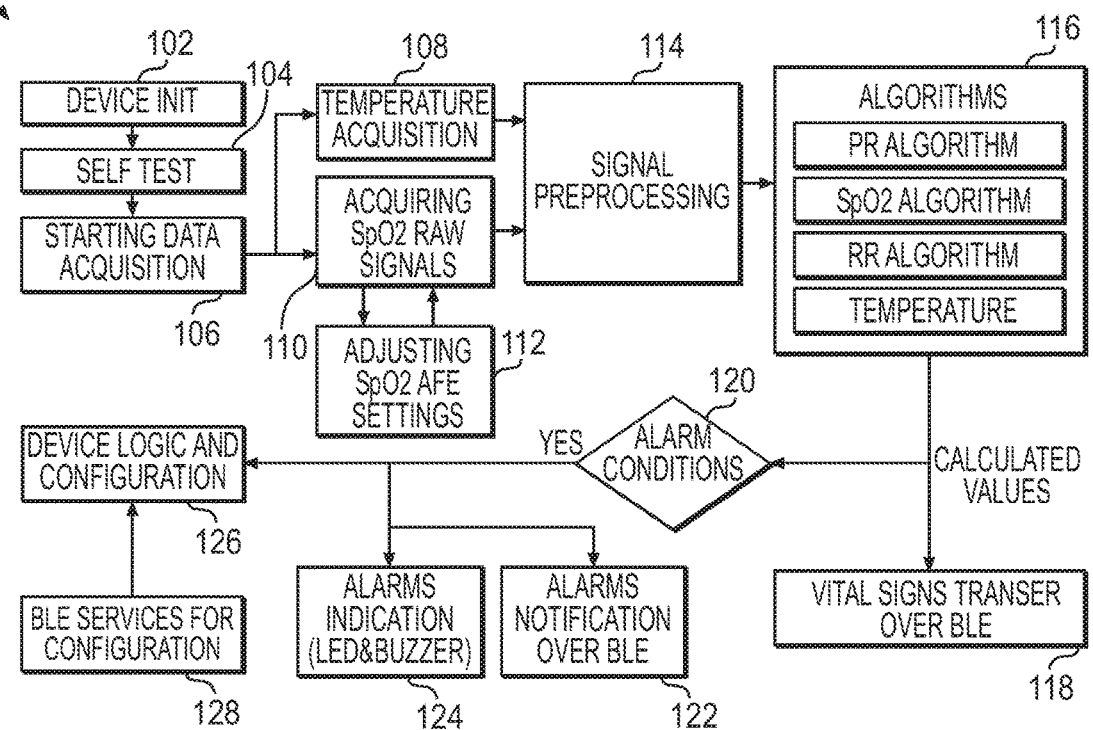
FIG. 9 is an exemplary electronic communications flow chart, according to aspects of the present disclosure.

FIG. 9 illustrates an exemplary flow chart for an activation and operation method 100 of wearable device 12 and its transmission of signals and data to the other elements of system 10. For example, wearable device 12 may be mounted on a patient, and in step 102, wearable device 12 may be powered on to facilitate device initialization. Once powered on, in step 104, wearable device 12 may load a predefined AFE configuration, alert parameters, and other operating details, and may also undergo a self-test. The self-test may ensure that temperature sensor 40, optical sensor 42, and the wireless communication elements (such as, e.g., wireless connectivity layer 76) are operating properly. Step 104 may include a sensor off detection module to check if the signals from the sensors are sufficient to perform the signal analysis. Sensor off detection module may run continuously and/or periodically while wearable device 12 is activated. For example, if the signal or the root mean square of the signal from optical sensor 42 is greater than a low threshold and less than a high threshold, the detection module may return a flag that the signal is valid and strong enough for data acquisition and peak detection based on the acquired data. However, if the signal or the root mean square of the signal from optical sensor 42 is below the low threshold, above the high threshold, or otherwise out of range, then the other processing modules discussed below may not be run until the detection module indicates that a valid signal is detected. Alternatively, if the signal or the root mean square of the signal from optical sensor 42 is below the low threshold, above the high threshold, or otherwise out of range, then the detection parameters may be adjusted in an effort to yield a stronger signal. For example, if the signal quality is too low, a user may increase the intensity of the emitted light to potentially yield a stronger signal. Moreover, a signal may be sent to user device 14 that the sensors are suitable for monitoring. The low threshold and the high threshold may be based on preexisting samples. Furthermore, during monitoring, the ranges may be adjusted (e.g., via user input) based on detected data and/or other user input, as will be described in further detail below.

Additionally or alternatively, a gain adjustment of the signal may be calculated. The calculated gain adjustment may then be compared to respective low and high thresholds to determine whether the signal is valid and strong enough for data acquisition and peak detection based on the acquired data.

If improperly operating, wearable device 12 may activate indicator 22 and/or transmit a signal to user device 14 to indicate that wearable device 12 is not operating properly. For example, wearable device 12 may have a low battery or may be unable to measure temperature, pulse rate, etc. due to improper positioning on the patient or an obstruction between the sensors and the patient's skin.

If operating properly, wearable device 12 may start data acquisition in step 106, and may activate both temperature sensor 40 and optical sensor 42. As mentioned, optical sensor 42 may utilize red, infrared, and/or green LEDs, and collect any or all resulting optical signals. The waveform generated from the red, infrared, or green signal may be processed in three different phases to generate an accurate respiratory rate (i.e., pre-processing, estimation of respiratory rate using different features, and combining respiratory rates to generate a single value to display). In step 108, temperature sensor 40 may acquire temperature data, and in step 110, optical sensor 42 may acquire $SpO_2$ raw data signals, which may be adjusted based on the AFE settings (as described above) in step 112.

In step 114, both the temperature data and the $SpO_2$ data and the corresponding signals may be preprocessed. The preprocessing may include inputting the raw data into a preprocessing module to filter and decimate the raw data. The raw data may be digitally filtered to separate typical pulse rate frequencies from typical respiratory rate frequencies. For example, for neonate patients, a typical pulse rate frequency range is approximately 1.67 to 2.67 Hz, and a typical respiratory rate frequency range is approximately 0.33 to 1.0 Hz. For pediatric patients, a typical pulse rate frequency range is approximately 1.17 to 1.83 Hz, and a typical respiratory rate frequency range is approximately 0.2 to 0.5 Hz. For adult patients, a typical pulse rate frequency range is approximately 1.0 to 1.67 Hz, and a typical respiratory rate frequency range is approximately 0.2 to 0.42 Hz.

The preprocessing module may output decimated and low pass filtered red and infrared signals from the optical data received from optical sensor 42. Alternatively, the preprocessing module may output decimated, low pass, and high pass filtered red and infrared signals received from optical sensor 42. The low pass and high pass filters may be adjusted or recalculated based on the values of the raw data, a sample rate of the raw data, and/or user input. Decimating and filtering the data may reduce the necessary memory and processing power to store and process the data. In one instance, the filtered data sample rate may be 100 Hz. The low pass filter may include a $300^{th}$ order filter with a cut off frequency off approximately 4 Hz, approximately 6 Hz, approximately 8 Hz, or approximately 10 Hz, and the high pass filter may include a $600^{th}$ order filter with a cut off frequency of approximately 0.5 Hz, approximately 0.3 Hz, or approximately 0.1 Hz. In one aspect, the filters and cut off frequencies may be adjusted based on the patient's age, weight, diagnosis, or other patient-specific details. In addition, the filters and cut off frequencies may be adjusted as part of an automatic calibration process that optimizes the signal strength and quality acquired from the patient's skin. The low pass filter and the high pass filter may cause slight delays of approximately 1.5 seconds and 3 seconds, respectively.

Then, the preprocessed data may be processed through algorithms in step 116. The algorithms may include a pulse rate algorithm, an $SpO_2$ algorithm, a respiratory rate algorithm, and a temperature algorithm. Based on the algorithms, values may be calculated for pulse rate, $SpO_2$, respiratory rate, and temperature. In step 118, these values may be transmitted or transferred from wearable device 12 to the other elements of system 10 over BLE network 20, and the other elements may further process, display, and store the values.

In step 120, each calculated value may be compared to a threshold or range, which may be preprogrammed or adjustably set (e.g., via a user) for a particular patient. If a calculated value is outside of the respective threshold or range, an alarm condition exists for that calculated value. If an alarm condition exists, an alarm notification may be transmitted over BLE network 20 in step 122, for example, to user device 14 and may be displayed or otherwise indicated by user device 14. Moreover, an alarm indication may be signaled on wearable device 12 in step 124. For example, indicator 22 may illuminate a solid red light or flash. Alternatively or additionally, wearable device 12 may sound a buzzer or other audible signal. The alarm indications (e.g., particular flash pattern or buzzer sound) on wearable device 12 and user device 14 may vary based on the type of alarm (e.g., temperature too high or too low, respiratory rate too high or too low, $SpO_2$ too high or too low, etc.). Additional alarm indications may indicate other system issues, such as, for example, low battery, sensor or wearable device 12 malfunction. These alarm indications may include an audible indication or a separate indicator light on wearable device 12 or user device 14. Furthermore, in step 126, signals may be transmitted to device logic and configuration unit, which may include storing information in a memory within wearable device 12. Lastly, in step 128, based on the signals to the device logic and configuration unit, wearable device 12 may request and/or receive information or update via BLE network 20. Moreover, as shown in FIG. 1, it is noted that wearable device 12 may transmit processed data to user device 14 for display regardless of whether an alarm condition exists.

Wearable device 12 may also include programming that includes a sleep mode between sensor data acquisition, for example, every 10 seconds, every 15 seconds, every 30 seconds, every minute, every five minutes, etc. Wearable device 12 may include a plurality of sleep modes, which may vary for different sensor and/or different vital sign parameters. For example, pulse rate may be measured every 10 seconds, and temperature may be measured every minute. Alternatively, wearable device 12, when activated, may continuously sense data with temperature sensor 40 and optical sensor 42 and transmit that data to user device 14.

Figure 10:
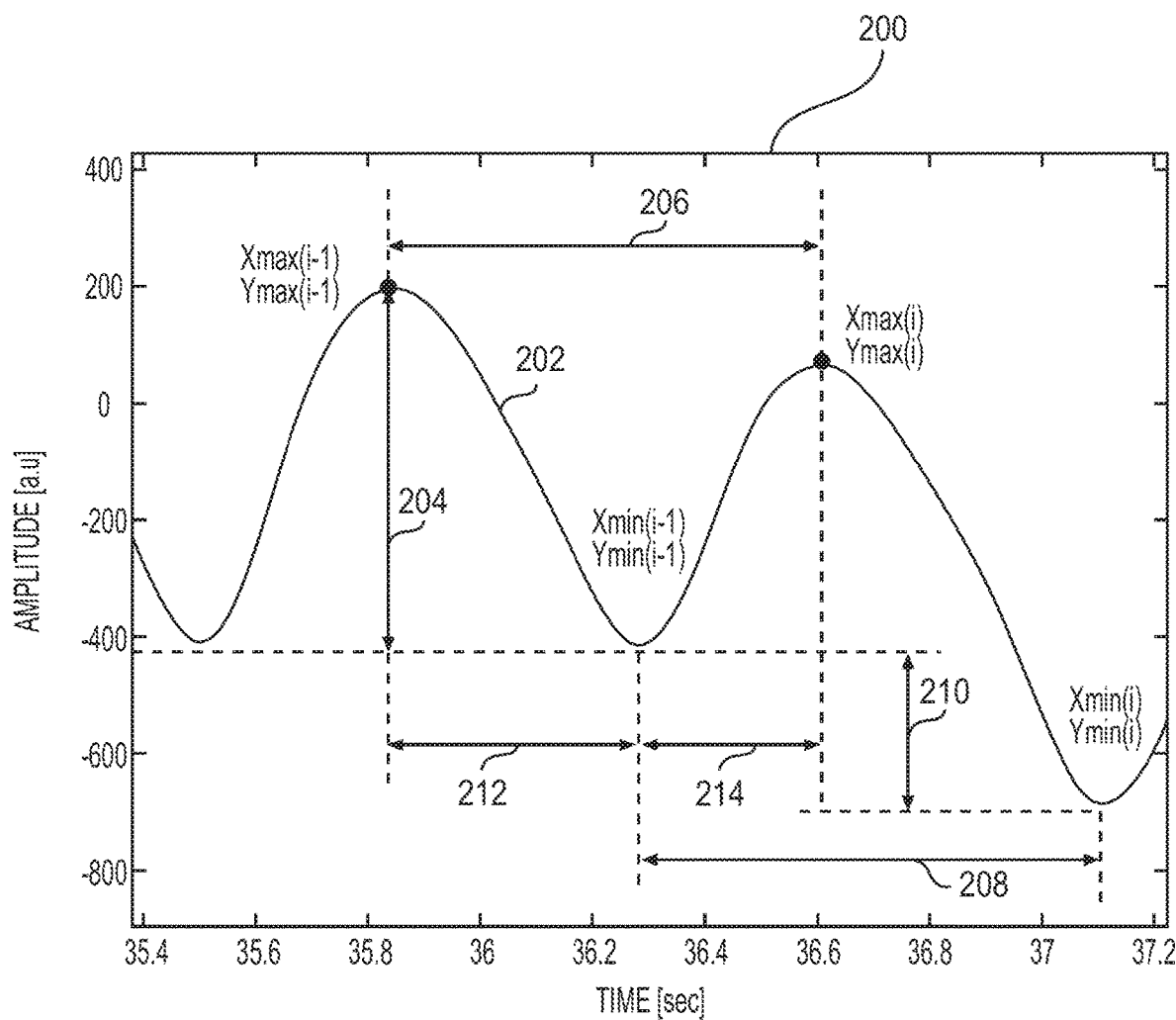
FIG. 10 illustrates an exemplary data waveform, according to aspects of the present disclosure.

FIG. 10 illustrates an exemplary graph 200 of pre-processed red or infrared optical sensor data 202 over time. For example, FIG. 10 illustrates a pulse amplitude 204, a peak-to-peak distance 206 between each peak, and a trough-to-trough distance 208 of the photoplethysmography readings over time, amongst other features. Wearable device 12 may determine a patient's pulse rate, respiratory rate, and blood oxygen saturation via a peak detection module which may analyze the pre-processed optical data from optical sensor 42. The analysis may be on a delay (e.g., seven seconds) from the time at which the wearable device 12 is activated. The peak detection module may use a peak detection algorithm, which may include a signal delay of approximately 0.3 seconds. The peak detection algorithm may detect local maxima ($X_{max}$, $Y_{max}$) and local minima ($X_{min}$, $Y_{min}$). The graph may be divided into a plurality of windows between local maxima and between local minima, which may reduce the probability of detecting a signal of a dicrotic notch. The results of the peak detection module may be validated and stored (e.g., values of 10 maxima and minima) in a local memory structure or in the memory within wearable device 12. It is noted that during inspiration, patients typically exhibit a temporary increase in pulse rate (often referred to as respiratory sinus arrhythmia or "RSA"), so averaging pulse rate data over a period of time may yield more reliable pulse rate readings.

A pulse extraction module may calculate an average pulse rate from the peak-to-peak distances 206 (FIG. 10). In one aspect, the following formula may be used to determine an average pulse over a period of time:

$$\text{Average Pulse} = \frac{60 \times Fs}{\text{Average } P2P}$$

In the above formula, Fs is the sample frequency, and Average P2P is the average distance between maximum peaks in a 10 second window. The Average P2P may be determined using the below formula:

$$\text{Average } P2P = \frac{1}{N}\sum_{i=0}^{N-1} p2pi$$

In the above formula, N is the number of peak-to-peak distances within the window or subset of data (e.g., 10 seconds), and p2p is the peak-to-peak distance between each peak, as shown by 206 between maxima and 208 between minima in FIG. 10. The formula is a summation of peak-to-peak distances from i=0 to i=N−1. The pulse extraction module yields an average pulse value. The pulse extraction module may also include a pulse update period defining a frequency of pulse value updating, which may update the pulse value each time a peak is detected. As such, the pulse rate may be based on an average of a continuously updated 10 second period. Furthermore, the pulse extraction module may include a validity defining parameter (e.g., 15 seconds may be the default), and if the time since the last detected valid value of the pulse rate is greater than the validity defining parameter, then the pulse extraction module outputs a signal that the pulse rate is not valid and may wait to output a pulse rate until sufficient values have been measured to display a valid average pulse rate. That is, the pulse extraction module may only output an average pulse rate value when it has obtained enough consistently valid pulse rate rates within a specified period of time (the validity defining parameter).

An $SpO_2$ extraction module may include an $SpO_2$ algorithm that uses peak positions from the peak detection module to calculate an R value from AC and DC components. For example, $$R = \frac{ACr}{DCr} \bigg/ \frac{ACir}{DCir}$$

In the above formula, ACr and DCr are the AC and DC components of a red channel, which is indicative of the red light detected by optical sensor 42. ACir and DCir are the AC and DC components of an infrared channel, which is indicative of the infrared light detected by optical sensor 42. Then, the $SpO_2$ extraction module may calculate the $SpO_2$ values using the following exemplary formula:

$$SpO_2 = 110 - (25 \times R)$$

The calculated $SpO_2$ values may be validated and stored in the $SpO_2$ extraction module or the memory within wearable device 12. A plurality of $SpO_2$ values over a period of time may be used to calculate an average $SpO_2$ value over the period of time, for example, 10 seconds. Furthermore, as with the pulse extraction module, the $SpO_2$ extraction module may also include an $SpO_2$ update period defining a frequency of $SpO_2$ value updating, which may update the $SpO_2$ value each time a peak is detected. As such, the $SpO_2$ may be based on an average of a continuously updated 10 second period. Furthermore, the $SpO_2$ extraction module may include a validity defining parameter (e.g., 15 seconds may be the default), and if the time since the last detected valid value of the $SpO_2$ is greater than the validity defining parameter, then the $SpO_2$ extraction module outputs a signal that the $SpO_2$ value is not valid and may wait to output a $SpO_2$ value until sufficient values have been measured to display a valid average $SpO_2$ value. That is, the $SpO_2$ extraction module may only output an $SpO_2$ value when it has obtained enough peak-to-peak data to determine an accurate average $SpO_2$ value.

A respiratory rate extraction module may include an algorithm to calculate a respiratory rate based on pulse amplitude variability ("PAV"). For example, $$PAV = y\max[i] - y\min[i]$$

In the above formula, $y_{max}[i]$ is a local maxima in the infrared photoplethysmography signal, and $y_{min}[i]$ is a local minimum in the infrared photoplethysmography signal. The PAV is shown as 204 in FIG. 10. It is noted that the PAV is simply one of a variety of manners in which the respiratory rate extraction module may calculate respiratory rate. In further arrangements, the respiratory rate extraction module may determine respiratory rate based on a change in amplitude between peaks, or a change in amplitude between valleys. In addition to PAV, pulse width variability (PWV), shown as 208 in FIG. 10, and the baseline minima variability (BMV), shown as 210, may also be useful in the respiratory rate calculation and/or additional calculations. For example, a time between a $x_{max}[i-1]$ and $x_{min}[i-1]$, shown as 212, as well as a time between $x_{min}[i-1]$ and $x_{max}[i]$, shown as 214, may provide useful information for further calculations because changes in the photoplethysmography waveform may vary from patient to patient as different patients may exhibit different variations in PAV, PWV, BMV, etc. A calibration factor may account for patient-to-patient variations, or a weighted combination of the variations may generate a patient's respiratory rate. In one instance, PAV values may be interpolated to a 10 Hz sampling rate, which converts the peak-to-peak measurements to a time domain. Then, the respiratory rate extraction module may perform a fast Fourier transform in a sliding window on one or more of the photoplethysmography signal features identified above. For example, the respiratory rate extraction module may perform the fast Fourier transform on a window of 30 seconds of PAV data, with a one second shift. The resulting transformed data may detect spectral maxima, which may be in a spectral range of approximately 0.08 Hz to approximately 0.8 Hz. It is noted that a continuous wavelet transform, neural networks, or other methods may be used to estimate the respiratory rate using photoplethysmography. The respiratory rate value may be calculated by converting the spectral maxima into the time domain by computing T=1/F and interpolating to a 10 Hz sampling rate.

The extracted respiratory rate values may be validated and stored in respiratory rate extraction module or the memory within wearable device 12. A plurality of respiratory rate values over a period of time may be used to calculate an average respiratory rate over the period of time, for example, 10 seconds. Furthermore, as with the pulse extraction module and the SpO$_2$ extraction module, the respiratory rate module may also include a respiratory rate update period defining a frequency of respiratory rate value updating, which may update the respiratory rate value each time a maxima or minima is detected. As such, the respiratory rate may be based on an average of a continuously updated 10 second period. Furthermore, the respiratory rate extraction module may include a validity defining parameter (e.g., 15 seconds may be the default), and if the time since the last detected valid value of the respiratory rate is greater than the validity defining parameter, then the respiratory rate extraction module outputs a signal that the respiratory rate value is not valid and may wait to output a respiratory rate value until sufficient values have been measured to display a valid average respiratory rate value. That is, the respiratory rate extraction module may only output a respiratory rate value when it has obtained sufficient maxima and minima data to determine an accurate average respiratory rate value.

It is further noted that the respiratory rate extraction module may extract the respiratory rate through other methods. For example, a weighted average of respiratory rate values may be used to determine a single respiratory rate value to display and use to alert determinations. Different patients exhibit variations in the photoplethysmography waveforms, so an exemplary respiratory rate algorithm may use a weighted average of the peak-to-peak values, the pulse amplitude variability, and the baseline minima variability.

A temperature measurement module may sample the data from temperature sensor 40 at a rate of approximately 1 Hz. The temperature measurement module may calculate temperature T in Celsius from the temperature signal, $T_{raw}$ according to the below formula:

$$T = (T_{raw} \times a) - b$$

In the above formula, a and b are calibration parameters that may vary or be adjusted based on the specific hardware. In one aspect, a=175/65536 and b=46.85. The aforementioned extracted and calculated values may be transmitted to a firmware module, which may be a part of MCU 70. The firmware module receives or has preprogrammed thresholds and/or ranges for each extracted and calculated value. The thresholds and/or ranges may be acquired over BLE network from user device 14 and/or the mobile application downloaded or otherwise running on user device 14. The thresholds and/or ranges for each extracted and calculated value may be adjustable via the mobile application, as discussed below with respect to FIG. 12, to be patient-specific, for example, based on age, weight, diagnosed illness, etc. The firmware module stores the thresholds and/or ranges internally or in the memory of wearable device 12. Firmware module may compare the extracted and calculated values for each aforementioned value with the respective threshold or range.

If an extracted or calculated value is above the respective threshold or outside of the respective range, firmware module activates an alarm mode. The alarm mode may include a local alarm indication on wearable device 12. As discussed, this local alarm indication may include activating indicator 22, e.g., a solid or flashing red LED, and/or an audible alarm (e.g., an audible signal emitting from either wearable device of user device 14). The alarm mode may also include transmitting alert data to user device 14 and/or to the mobile application. User device 14 and/or the mobile application may display the alarm notification and/or activate an audible or tactile alarm. The alarm mode may remain active until the vital sign(s) causing the alarm mode return to below the threshold or within the range. Alternatively, a user may input a mute and/or reset command. This command may be input by action on user device 14, the mobile application, or by direct action on wearable device 12.

For example, the calculated temperature may be rounded to the nearest hundredth and transmitted to MCU to determine whether alarm conditions exist. The calculated temperature, with or without an alarm notification, may also be transmitted to user device 14. The calculated temperature may be stored in the temperature measurement module or in the memory of wearable device 12. The calculated temperature may be transmitted and/or displayed without averaging. Alternatively or additionally, an average temperature over a period of time may be transmitted, stored, and/or displayed.

Figure 11:
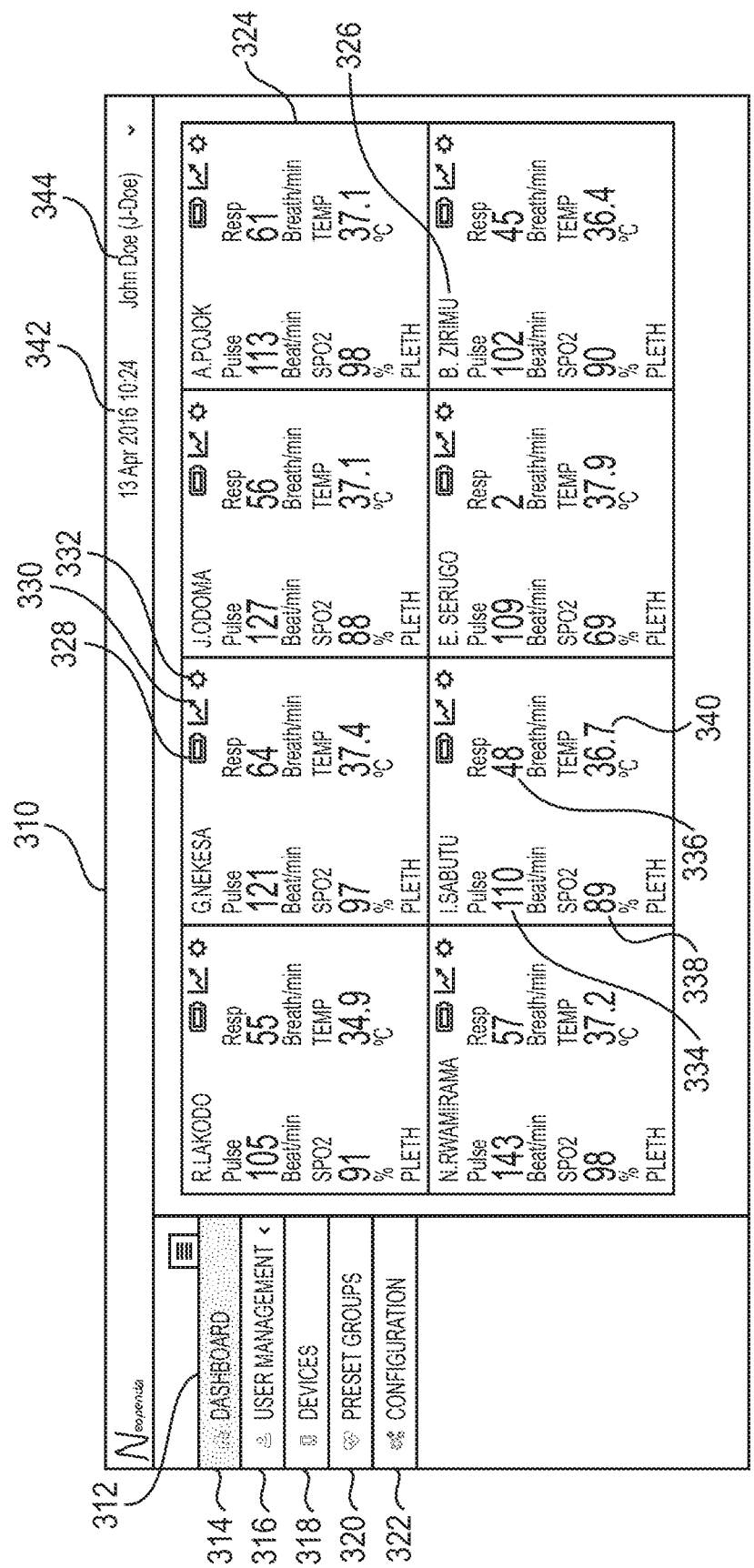
FIG. 11 illustrates an exemplary user interface display, according to aspects of the present disclosure.
Figure 12:
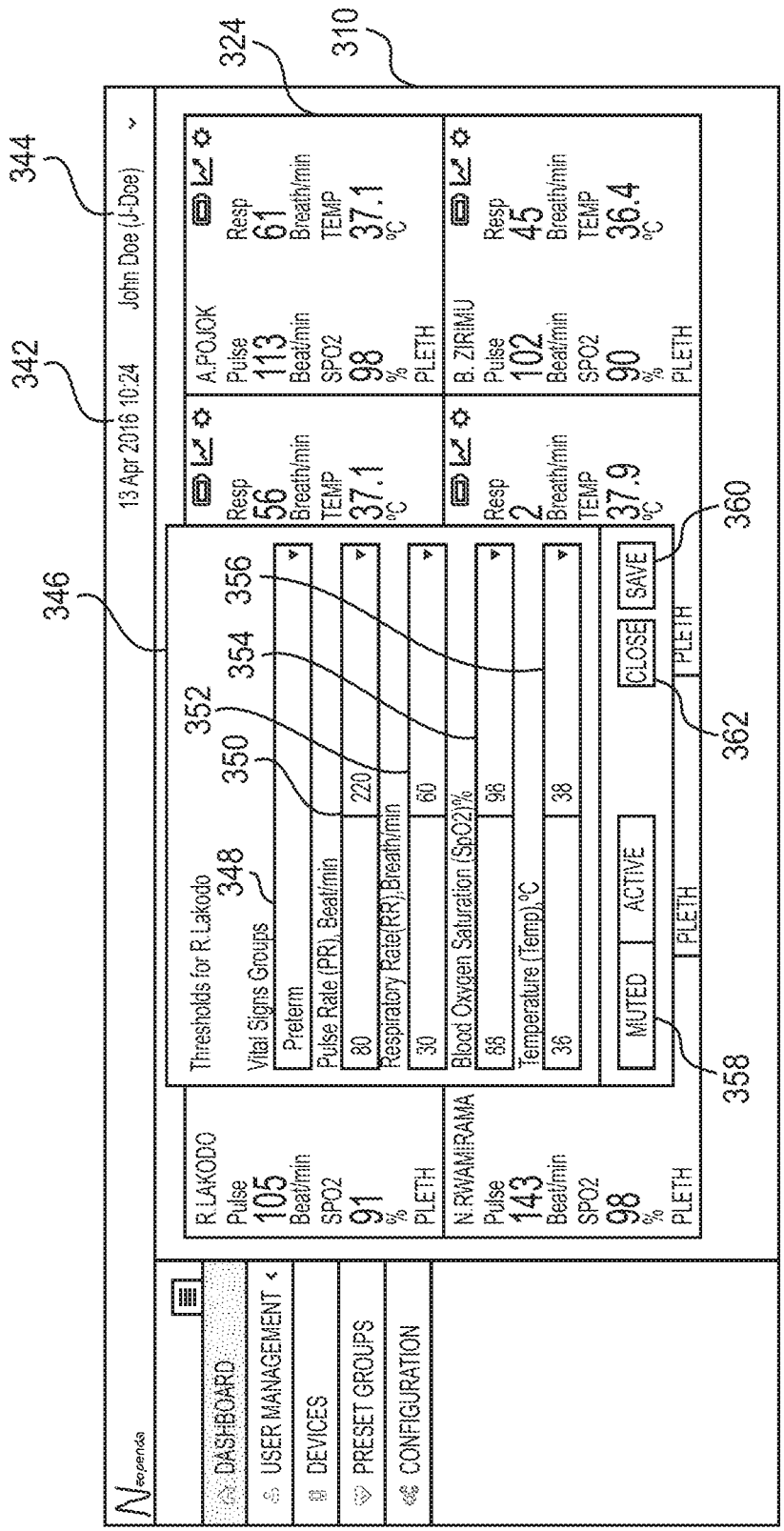
FIG. 12 illustrates an exemplary feature of the user interface display, according to aspects of the present disclosure.
Figure 13:
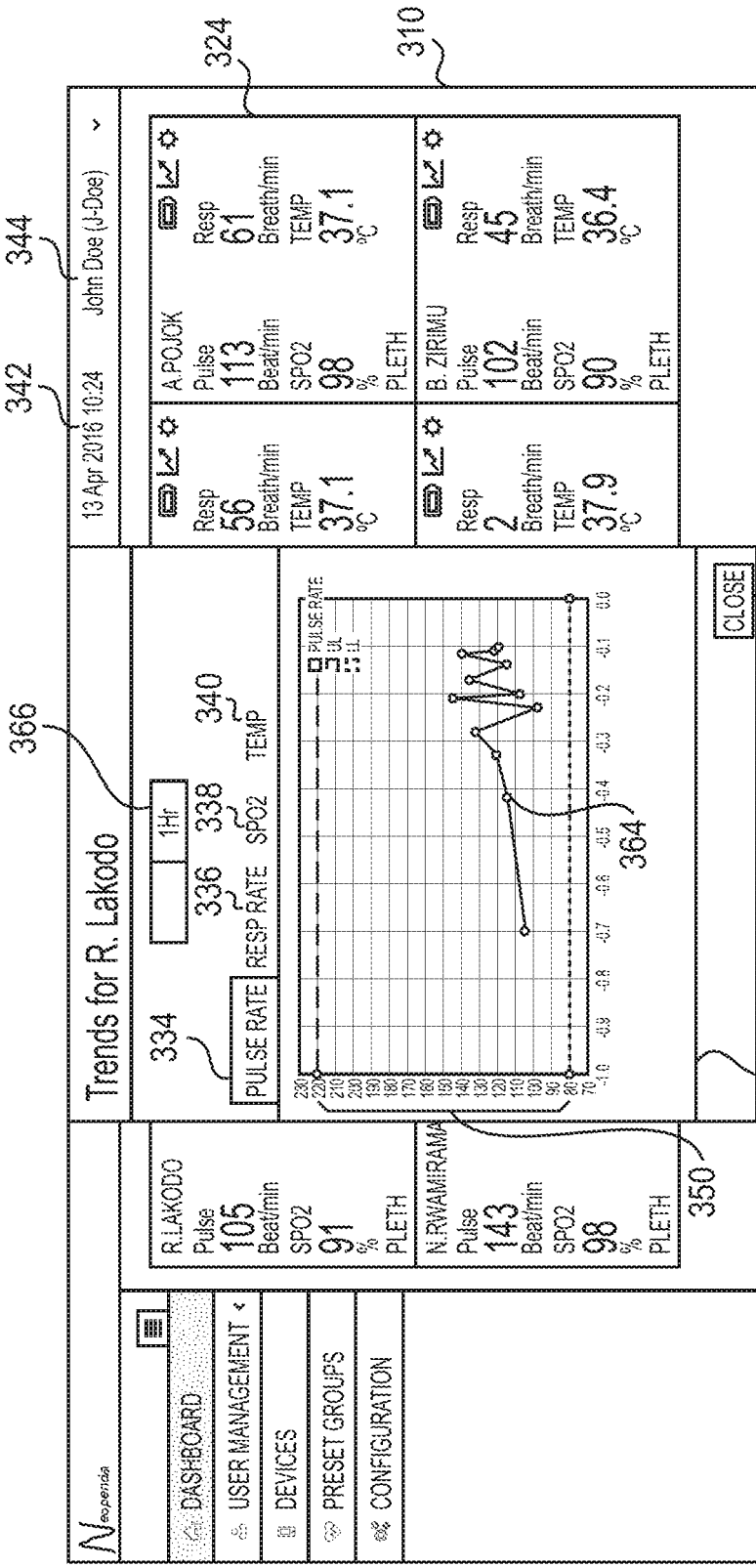
FIG. 13 illustrates a further exemplary feature of the user interface display, according to aspects of the present disclosure.

Turning now to FIGS. 11-13, these figures illustrate aspects of the mobile application that may be implemented and displayed on display 24 of user device 14. In this aspect, the mobile application may be an application run on a computer, smartphone, tablet, etc., and the mobile application may also be a web application deployed on a desktop computer, laptop computer, or another electronic display. As shown in FIG. 11, the mobile application may include a user interface 310. User interface 310 may include a list 312 of tabs, which may include a dashboard 314, a user management tab 316, a devices tab 318, a preset groups tab 320, and a configuration tab 322. Each of the tabs in list 312 may include a different display on user interface 310, which may allow the user to view information related to a plurality of wearable devices 12, and to modify the settings, alarm thresholds, etc.

With dashboard 314 selected, user interface 310 may include a plurality of patient displays 324, and each patient display 324 may display current biometric data for each patient measured by respective wearable devices 12. For example, patient display 324 may display the name 326 of the patient associated with each wearable device 12, a current battery charge level 328 for each wearable device 12, a link to view historical trend data from the patient's wearable device 330, and a link to view or edit the patient's information 332. Patient display 324 may also display a name of a relative of the patient, a bed number, or any other information indicative of the patient's identity or location. Patient display 324 may also display an indicator of the operational status of the wearable device, and a warning in the event that the connection to the wearable device is lost and/or data has ceased transmitting. Patient display 324 may also display real-time information on a pulse rate 334, a respiratory rate 336, an SpO$_2$ percentage 338, and a body temperature 340. The real-time information may be extracted and/or calculated based on the processed data obtained from temperature sensor 40 and optical sensor 42 as discussed above. In addition, user interface 310 may include a time and date 342 and a user profile 344 identifying the user, for example, a specific medical professional tasked with caring for the patients wearing wearable devices 12. Furthermore, patient display 324 may include an option to display the current photoplethysmography waveform for each patient.

It is noted that while only eight patient displays 324 are displayed in FIG. 11, dashboard 314 on user interface 310 may display up to 15 patient displays 324, up to 30 patient displays 324, up to 50 patient displays 324, etc. For example, user interface 310 may continuously cycle through a series of dashboards 314 to display all the patient displays 324. Alternatively, user interface 310 may selectively display a subset of patient displays 324, for example, patient displays 324 with alarm conditions or conditions that are within a specified range of being an alarm condition. Moreover, a user may scroll or toggle through the plurality of dashboards 314 to display all the patient displays 324.

If one of pulse rate 334, respiratory rate 336, SpO$_2$ percentage 338, or body temperature 340 exceeds a programmed threshold or is outside of a programmed range, patient display 324 may indicate an alert. The alert may be in the form of a flashing light, flashing numerals, or a change in color of the numerals for the specific biometric parameter. Alternatively or additionally, user device 14 may include an audible or vibratory alert. These alerts may be based on both the received processed data and the alert data.

FIG. 12 illustrates a patient-specific profile 346. In one instance, a user may click on or otherwise select a particular patient display 324 or link 332 to display patient-specific profile 346. Patient-specific profile 346 may display a series of drop-down selections, which may allow the medical professional to select a preset vital sign group 348. Each vital sign group 348 may include a plurality of thresholds or ranges for a variety of biometric data, including, e.g., a pulse rate range 350, a respiratory rate range 352, a blood oxygen saturation (SpO$_2$) range 354, and/or a temperature range 356. The biometric data and/or the thresholds or ranges may vary based on which vital sign group 348 is selected. For example, if "preterm" is selected, pulse rate range 350 may be between 80 and 220 beats per minute, respiratory rate range 352 may be between 30 and 60 breaths per minute, blood oxygen saturation (SpO$_2$) range 354 may be between 88% and 98%, and temperature range 356 may be between 36° C. and 38° C. Additional vital sign groups 348 include "term," <30 weeks, 30-34 weeks, 34-38 weeks, 38-42 weeks, etc. Each range may be further manually adjustable via a drop-down selection or direct editing, or may be locked based on a user's profile or a pre-programmed setting. Furthermore, each patient-specific profile 346 may include a mute button 358, which may be toggled between "muted" and "active" settings to selectively activate or deactivate the sensor monitoring and alarms associated with that patient and wearable device 12. The patient-specific profile 346 may also include editable information fields such as the patient's full name and display name, the date of birth, the birth weight, and diagnosis at admission. Lastly, patient-specific profile 346 may include a save button 360 to store the selected setting and a close button 362 to return to user interface 310 displaying the plurality of patient displays 324.

FIG. 13 illustrates an additional feature of user interface 310. As shown, user interface 310 may include graphical representations 363 of the data obtained from temperature sensor 40 and optical sensor 42. For example, user interface 310 may include a graph 364 of the pulse rate 334 data over time. Such a graph may be created or accessed by, for example, a user selecting the pulse rate 334 icon/tab. The graph 364 may include plots of the instantaneous pulse rate 334 readings, along with the upper and lower limits of the pulse rate range 350 selected in the vital sign group 348 as shown in FIG. 12. The time period displayed on graph 364 may be selectable via time period tab 366. In one aspect, graph 364 may display the obtained data for the past hour, two hours, 4 hours, 24 hours, etc. Graph 364 may similarly display the data for respiratory rate 336, the data for SpO$_2$ 338, and/or the data for temperature 340. Graph 364 may display the respective data separately, or graph 364 may display the data for particular measurements simultaneously with the respective plots overlaid. Graphical representation 363 may include a close button 368 to return to user interface 310 displaying the plurality of patient displays 324. Graphical representation 363 may also include a feature to allow a user to enter an "event" for a period or periods of time when detected vital signs are out of the respective ranges. Graphical representation 363 may include additional notifications, for example, if the alarm notification is not turned off or otherwise addressed after 20 seconds, 1 minute, 5 minutes, 10 minutes, etc.

Moreover, user interface 310 may include a plurality of user logins, which may be accessible via user management tab 316. In one aspect, each medical professional at a hospital may have a personal user login. A subset of patient displays 324 may be displayed for one user, while the full plurality of patient displays 324 may be displayed for another user. Additionally or alternatively, only a subset of users may be granted access to adjust patient-specific profiles 346 as discussed above with respect to FIG. 12. Furthermore, user management tab 316 (FIG. 11) may allow select users to modify the access settings for other users. User interface 310 may also allow a new medical professional to create a new user login, with the settings and access parameters being customizable. User interface 310 may store each user's login and logout times and log any changes that they make to user and patient accounts.

Historical data for each patient may be stored in the mobile application. For example, devices tab 318 (FIG. 11) may display a list of wearable devices 12, with each wearable device 12 being individually selectable such that a user may view the historical data for that wearable device 12 for a particular time period. Additionally or alternatively, such historical data (FIG. 13) may be accessible from the Dashboard by selecting icon 330. Such information may be useful in the event of an alarm condition in order to study and/or diagnose a potential cause of the alarm condition and/or a trend of alarm conditions.

Preset groups tab 320 may allow a user to view or create a group of wearable devices 12. A user may select a subset of wearable devices 12 and create a dashboard setting to only view that subset of patient displays 324. For example, a user may sort the patient displays 324 by patient age, diagnosis, average pulse rate, etc. in order to quickly view patients with potentially riskier conditions. Preset groups tab 320 may also allow users to modify, delete, or add preset vital signs thresholds, such as for "preterm" and "term" groups.

Configurations tab 322 may allow a user or a select group of users to modify the settings of user interface 310. For example, a user may change the color scheme, add or remove wearable devices 12 from dashboard 314, etc. In one instance, configurations tab 322 may allow a user to sync his or her smartphone, smartwatch, tablet, or other mobile device with user interface 310 to view patient displays 324 and receive alert signals on the mobile device. In the configurations tab 322 a user may also control data backup and export settings.

Figure 14:
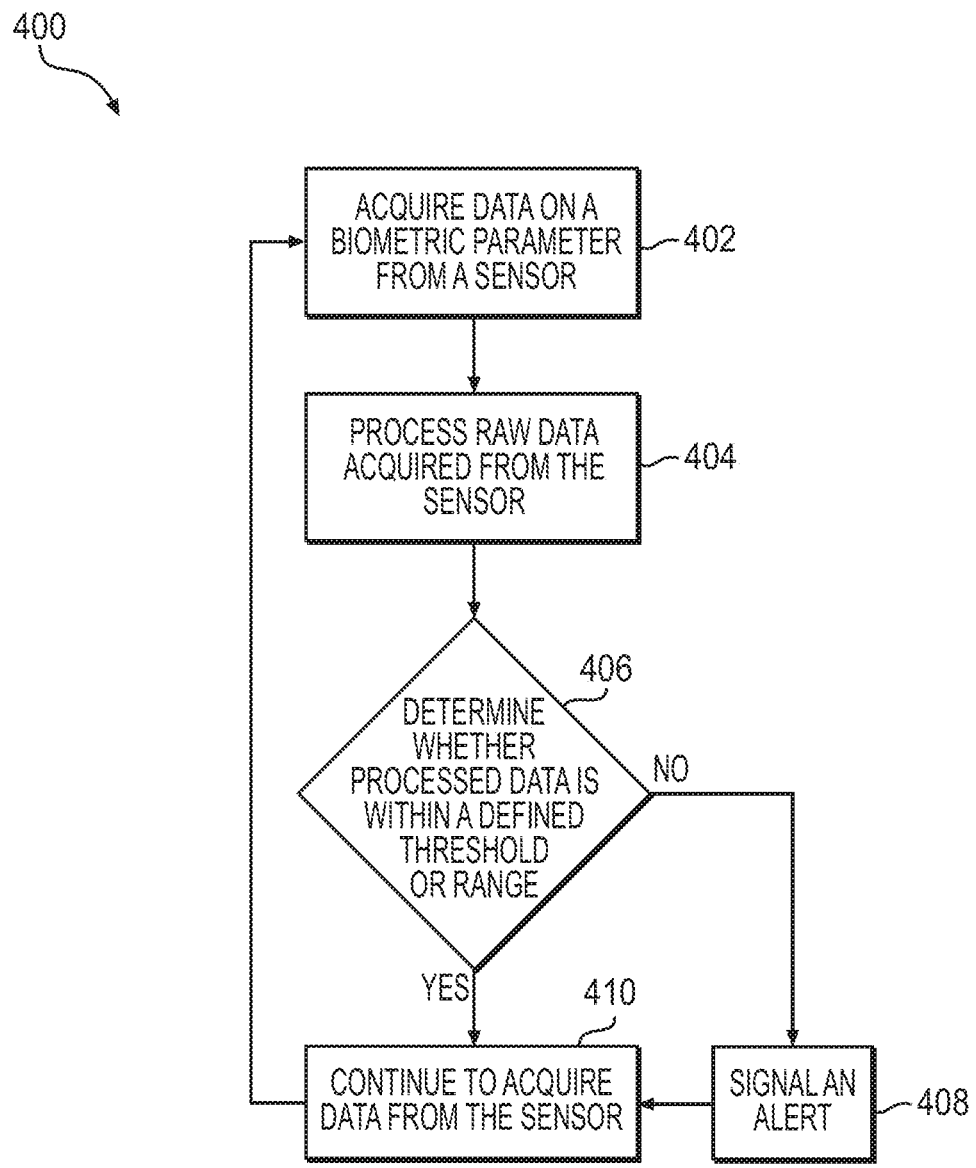
FIG. 14 is a flow chart portraying an exemplary monitoring method, according to aspects of the present disclosure.

According to one aspect, FIG. 14 depicts a flow diagram of an exemplary method for electronically monitoring a patient and signal an alert using wearable device 12 and the other components of system 10. For example, as detailed in FIG. 14, system 10 may continuously or periodically perform method 400 to monitor the biometric information of a plurality of patients. Step 402 may include acquiring data on a biometric parameter from a sensor. This may include wearable device 12 activating temperature sensor 40 and optical sensor 42. The data acquisition step may be preceded by a device initialization and/or a self test process, as discussed above. The biometric parameter may be raw data related to body temperature, pulse rate, respiratory rate, and/or $SpO_2$. Step 404 may include processing the raw data acquired from the sensor. As discussed above, the raw data may be processed internal to wearable device 12, for example, by a microcontroller unit 70 and/or other internal components 52 on printed circuit board 56. Processing the raw data may yield values for the patient's skin temperature, pulse rate, respiratory rate, and/or $SpO_2$.

Then, in step 406, system 10 may determine whether the processed data is within a defined threshold or range. For example, the patient's body temperature may be compared to a specific programmed or otherwise set temperature range. If the processed data is not within a defined the threshold or range, system 10 may signal an alert, as shown in step 408. The alert may be signaled via one or both of wearable device 12 and user device 14, and the signal alert may include visual indications, e.g., flashing of indicator 22 or of patient display 324, and may further include audible or vibratory signals to the user that the biometric parameter is in alert mode. If the processed data is within the defined threshold or range, then system 10 may continue to acquire data from the sensor in step 410. Even if an alert is signaled in step 408, system 10 may continue to acquire data from the sensor. Moreover, wearable device 12 may transmit the acquired and processed data to user device 14 over BLE network 20.

It is understood that the above method 400 may be performed for each of temperature sensor 40 and optical sensor 42, as well as each biometric parameter discussed above. Furthermore, it is noted that the sensed data may be transmitted to the other devices in system 10 to be further analyzed, displayed, and/or stored. Alternatively, the raw data may be transmitted to user device 14 for processing.

In a further aspect, system 10 may include a plurality of wearable devices 12 positioned on multiple body parts of at least one patient. For example, one wearable device 12 may be positioned on a patient's forehead, and another wearable device 12 may be positioned on the patient's finger and/or toe. The two wearable devices 12 may transmit and receive signals to and from each other, and may cross-reference the biometric parameters each wearable devices 12 measure and coordinate alert signals. For example, if the patient's forehead wearable device 12, which acquires optical data based on reflective measurements, indicates an alert, but the finger wearable device 12, which acquires optical data based on transmission measurements, system 10 may not indicate an alert until both wearable devices 12 indicate an alert based on their respective sensor measurements. Alternatively, the two wearable devices 12 may both indicate an alert if only one wearable device 12 senses an alert situation based on the sensor measurements. It is noted that one or more wearable device(s) 12 may be positioned on a patient's arm, chest, leg, etc.

The system 10 and methods 100, 400 discussed above may help to improve patient care, especially in situations that may have significantly more patients than medical professionals. For example, in many developing countries, hospitals may be understaffed, underfunded, and/or experience intermittent power supplies. The systems and methods may allow one or a few medical professionals to reliably monitor several patients simultaneously (e.g., at least 5, at least 15, or at least 50 patients). In one aspect, wearable devices 12 may be mounted on neonatal patients in a neonatal care unit. The wearable devices 12 continuously monitor the body temperature, pulse rate, respiratory rate, and $SpO_2$ measurements for each patient. Then, a medical professional may monitor the measurements via user device 14. If one of the patients indicates a potentially problematic vital sign, then both wearable device 12 and user device 14 may alert the medical professional of which patient is experiencing the problem. Moreover, the particular vital sign may indicate to the medical professional a likely cause or causes of the problematic vital sign, which may help diagnose and/or treat the patient more quickly. Further, system 10 and methods 100, 400 discussed above may enable a device having only two sensors to accurately and reliably monitor and alert users, in real-time, to changes in at least three or at least four vital signs of a plurality of patients.

It is also noted that the systems and methods discussed above may be applicable to other situations. System 10 and methods 100, 400 may be used outside of hospitals, for example, in a home to track vital signs for an infant or young child who requires additional monitoring. Alternatively, system 10 and methods 100, 400 may be used to monitor patients undergoing or recovering from a surgery, geriatric patients in, for example, a nursing home or other assisted care facility, prisoners in a prison, and/or athletes engaged in high endurance training or competition. System 10 and methods 100, 400 may include machine learning algorithms in order to aid in diagnosis various conditions based on the detected vital signs, such as pneumonia. System 10 may also measure percent changes in vital sign activity, or deviations from a baseline or threshold in vital sign activity. System 10 may activate an alarm if the percent changes or deviations exceed the preset values.

Moreover, system 10 and methods 100, 400 may be further modified to include additional capabilities. For example, wearable device 12 may include a noninvasive subcutaneous optical bilirubin sensor to diagnosis jaundice and/or manage jaundice treatments. Wearable device 12 may include a surface skin conductance sensor to detect a patient's sweat release, which may be relevant in the diagnosis and management of several neonatal pathophysiologies such as Neonatal Abstinence Syndrome. Wearable device 12 may also include and/or modify optical sensor 42 to continuously and noninvasively measure a patient's blood pressure or other vital signs. Additionally, wearable device 12 may include a mechanism to stimulate the patient, for example, to provide tactile stimulation with vibration if the patient is experiencing apnea or another medical issue. System 10 may also track the activity of the patient, for example, by determining whether the patient is asleep or awake based on the measured vital signs, and by determining the activity levels in both a sleep state and an awake state.

Other embodiments of the present disclosure will be apparent to those skilled in the art from consideration of the specification and practice of the embodiments disclosed herein. While certain features of the present disclosure are discussed within the context of exemplary systems, devices, and methods, the disclosure is not so limited and includes alternatives and variations of the examples herein according to the general principles disclosed. It is intended that the specification and examples be considered as exemplary only, with a true scope and spirit of the present disclosure being indicated by the following claims.

What is claimed is:

1. A medical device, comprising
a temperature sensor configured to deliver a temperature signal;
an optical sensor configured to deliver an optical signal;
a microcontroller configured to receive the temperature signal and the optical signal, wherein the microcontroller is configured to calculate, in real-time, a skin temperature, a pulse rate, a respiratory rate, and a blood oxygen concentration based on the received temperature signal and the received optical signal, and wherein the microcontroller is configured to signal an alert if the skin temperature, the pulse rate, the respiratory rate, or the blood oxygen concentration is outside of a preset range, the preset range being programmed in a memory for the microcontroller according to a pediatric age, and for a neonatal patient, based on whether the neonatal patient was born premature or full term;
an indicator configured to indicate the alert, based on one or more of the skin temperature, the pulse rate, the respiratory rate, and the blood oxygen concentration;
a single housing containing the temperature sensor, the optical sensor, analog front-end circuitry in communication with the optical sensor and the microcontroller, the microcontroller, and the indicator, the single housing including at least one housing opening for operably positioning the temperature sensor, the optical sensor, or both, in contact with and/or facing a forehead of a neonate or pediatric patient; and
a reusable strap connected to the single housing, the strap having:
an adjustable length that is configured to retain the at least one housing opening in contact with and/or facing the forehead of the neonate or pediatric patient;
a strap opening that overlaps the at least one housing opening;
a widened portion in the strap that defines the strap opening, the widened portion being sized to receive the single housing;
a first arm that extends from a first end of the widened portion; and
a second arm that extends from a second end of the widened portion, the second end being disposed opposite the first end.

2. The medical device of claim 1, further comprising a transmitter unit within the housing, wherein the transmitter unit is configured to transmit signals over a Bluetooth low energy network to at least one of a user device, a server, or a database.

3. The medical device of claim 1, wherein the single housing includes a first case portion and a second case portion, the second case portion including:
the at least one housing opening for operably positioning the temperature sensor, the optical sensor, or both, in contact with and/or facing the forehead of the neonate patient or the pediatric patient.

4. The medical device of claim 3, wherein the microcontroller is programmed to cause the indicator to generate a light to indicate the alert, based on the preset range.

5. The medical device of claim 1, wherein the microcontroller is powered by a battery, and wherein the medical device further comprises a battery level indicator.

6. A medical system, comprising
a plurality of medical devices according to the medical device of claim 1, a first medical device of the plurality of medical devices being configured to be positioned proximate skin of a first patient, and a second medical device of the plurality of medical devices being configured to be positioned proximate skin of a second patient; and
a user device,
wherein each of the plurality of medical devices and the user device transmit and receive signals via a low energy network, wherein at least the first and second medical devices include a threshold or range for at least one patient-specific biometric data measurement, and wherein the threshold or range is adjustable by the user device.

7. The medical system of claim 6, wherein the user device includes a user interface with a dashboard, and wherein the dashboard displays the patient-specific biometric data received from the plurality of medical devices.

8. The medical system of claim 6, wherein at least one of the plurality of medical devices and the user device includes the threshold or range for each patient-specific biometric data measurement.

9. The medical system of claim 8, wherein, in response to a determination that the patient-specific biometric data measurement exceeds or is outside of the respective threshold or range, then at least one of a medical device of the plurality of medical devices and the user device indicate an alert.

10. The medical system of claim 9, wherein the alert is an indicator light generated by the indicator of the medical device.

11. The medical system of claim 9, wherein the alert is an audible alarm signaled on the user device.

12. The medical system of claim 9, wherein the alert is also sent to an additional device via the low energy network or as an SMS signal.

13. The medical device of claim 1, wherein the analog front-end circuitry in the single housing includes an electronic filter configured to preprocess the optical signal for a neonatal patient to separate a frequency range of approximately 1.67 Hz to approximately 2.67 Hz to identify a neonatal pulse rate from the optical signal, from a frequency range of approximately 0.33 Hz to approximately 1.0 Hz to identify a neonatal respiratory rate from the optical signal.

14. A method, comprising:
acquiring patient-specific biometric data from a plurality of wearable medical devices,
wherein the plurality of medical devices each include:
a temperature sensor configured to deliver a temperature signal;
an optical sensor configured to deliver an optical signal;
a microcontroller configured to receive the temperature signal and the optical signal, wherein the microcontroller is configured to calculate, in real-time, a skin temperature, a pulse rate, a respiratory rate, and a blood oxygen concentration based on the received temperature signal and the received optical signal, and wherein the microcontroller is configured to signal an alert if the skin temperature, the pulse rate, the respiratory rate, or the blood oxygen concentration is outside of a preset range, the preset range being programmed in a memory for the microcontroller and associated with a pediatric age, and for a neonatal patient, based on whether the neonatal patient was born premature or full term;
an indicator configured to indicate the alert, based on one or more of the skin temperature, the pulse rate, the respiratory rate, and the blood oxygen concentration;
a single housing containing the temperature sensor, the optical sensor, analog front-end circuitry in communication with the optical sensor and the microcontroller, the microcontroller, and the indicator, the single housing including at least one housing opening for operably positioning the temperature sensor, the optical sensor, or both, in contact with and/or facing a forehead of a neonate or pediatric patient; and
a reusable strap connected to the single housing, the strap having an adjustable length that retains the at least one housing opening in contact with and/or facing the forehead of the neonate or pediatric patient, the strap having:
a strap opening that overlaps the at least one housing opening;
an adjustable length that retains the at least one housing opening in contact with and/or facing the forehead of the neonate or pediatric patient; and
a widened portion in the strap that defines the strap opening, the widened portion being sized to receive the single housing,
wherein each wearable medical device is positioned on a neonatal or pediatric patient, and wherein each wearable medical device includes the temperature sensor and the optical sensor, the temperature sensor and the optical sensor being positioned proximate skin of the patient, and wherein the temperature sensor and the optical sensor acquire the patient-specific biometric data in real-time;
processing the data acquired from the temperature sensor and the optical sensor;
determining whether the processed data is within the preset range, based on the neonatal or pediatric age; and
signaling an alert when the processed data is not within the preset range.

15. The method of claim 14, further comprising, wherein if the processed data is within the preset range, continuing to acquire data from the sensor.

16. The method of claim 14, wherein the alert is signaled on the wearable medical device.

17. The method of claim 14, wherein the alert is signaled on a user device.

18. A method, comprising:
generating patient-specific biometric data with one or more wearable medical devices that include:
a temperature sensor configured to deliver a temperature signal;
an optical sensor configured to deliver an optical signal;
a microcontroller configured to receive the temperature signal and the optical signal, wherein the microcontroller is configured to calculate, in real-time, a skin temperature, a pulse rate, a respiratory rate, and a blood oxygen concentration based on the received temperature signal and the received optical signal, and wherein the microcontroller is configured to signal an alert if the skin temperature, the pulse rate, the respiratory rate, or the blood oxygen concentration is outside of a preset range, the preset range being programmed in a memory for the microcontroller and associated with a neonatal age, and for a neonatal patient, based on whether the neonatal patient was born premature or full term;
an indicator configured to indicate the alert, based on one or more of the skin temperature, the pulse rate, the respiratory rate, and the blood oxygen concentration;
a single housing containing the temperature sensor, the optical sensor, analog front-end circuitry in communication with the optical sensor and the microcontroller, the microcontroller, and the indicator, the single housing including at least one housing opening for operably positioning the temperature sensor, the optical sensor, or both, in contact with and/or facing a forehead of a neonate or pediatric patient; and
a reusable strap connected to the single housing, the strap having an adjustable length that retains the at least one housing opening in contact with and/or facing the forehead of the neonate or pediatric patient, the strap having:
a strap opening that overlaps the at least one housing opening;
an adjustable length that retains the at least one housing opening in contact with and/or facing the forehead of the neonate or pediatric patient; and
a widened portion in the strap that defines the strap opening, the widened portion being sized to receive the single housing;
wherein the one or more wearable medical devices are positioned on a neonatal or pediatric patient and include the temperature sensor and the optical sensor, the temperature sensor and the optical sensor being positioned proximate skin of the patient, and wherein the temperature sensor and the optical sensor acquire the patient-specific biometric data in real-time;
processing the data acquired from the temperature sensor and the optical sensor, including processing the optical signal for a neonatal patient to separate a frequency range of approximately 1.67 Hz to approximately 2.67 Hz to identify a neonatal pulse rate from the optical signal, from a frequency range of approximately 0.33

Hz to approximately 1.0 Hz to identify a neonatal respiratory rate from the optical signal;
determining whether the processed data is within the preset range based on the neonatal or pediatric age; and
signaling an alert when the processed data is not within the preset range.

19. The method of claim 18, wherein the strap is removably connected to the single housing and includes a silicone material.

20. The method of claim 19, wherein the strap includes a first arm that extends from a first end of the widened portion and a second arm that extends from a second end of the widened portion, the second end being disposed opposite the first end, the first arm having a length that is more than twice as long as a length of the second arm.

* * * * *